(12) United States Patent
Hiejima et al.

(10) Patent No.: US 8,052,641 B2
(45) Date of Patent: Nov. 8, 2011

(54) INDWELLING NEEDLE WITH WINGS

(75) Inventors: Katsuhiro Hiejima, Osaka (JP);
Yukinori Ebara, Osaka (JP)

(73) Assignee: NIPRO Corporation, Osaka (JP)

( * ) Notice: Subject to any disclaimer, the term of this patent is extended or adjusted under 35 U.S.C. 154(b) by 129 days.

(21) Appl. No.: 12/308,508

(22) PCT Filed: Jun. 7, 2007

(86) PCT No.: PCT/JP2007/061515
§ 371 (c)(1),
(2), (4) Date: May 5, 2009

(87) PCT Pub. No.: WO2008/001590
PCT Pub. Date: Jan. 3, 2008

(65) Prior Publication Data
US 2010/0234804 A1    Sep. 16, 2010

(30) Foreign Application Priority Data

Jun. 30, 2006  (JP) ................................. 2006-181698

(51) Int. Cl.
*A61M 5/00*    (2006.01)
(52) U.S. Cl. ....................................... 604/110; 604/263
(58) Field of Classification Search .................. 604/110, 604/263, 264, 192–198, 177
See application file for complete search history.

(56) References Cited

U.S. PATENT DOCUMENTS

| | | | |
|---|---|---|---|
| 4,935,012 A | 6/1990 | Magre et al. | 604/192 |
| 7,010,344 B2 * | 3/2006 | Burnes et al. | 607/4 |
| 7,018,344 B2 * | 3/2006 | Bressler et al. | 604/177 |
| 7,294,118 B2 * | 11/2007 | Saulenas et al. | 604/110 |
| 2004/0181173 A1 | 9/2004 | Wilkinson | 600/576 |

FOREIGN PATENT DOCUMENTS

| | | |
|---|---|---|
| EP | 0 566 769 A1 | 10/1993 |
| JP | 10-085333 A | 4/1998 |
| JP | 2002-345955 A | 12/2002 |
| JP | 2003-116996 A | 4/2003 |
| JP | 2004-275741 A | 10/2004 |

* cited by examiner

*Primary Examiner* — Matthew F Desanto
(74) *Attorney, Agent, or Firm* — Kubovcik & Kubovcik

(57) ABSTRACT

There is provided a winged indwelling needle for reducing the possibility of damaging a blood vessel or the like by a cannula, including a movable unit 1 having the cannula and a hub, a tube 2 connected to the rear portion of the hub, a holder 3, and a fixing wing 4, in which the movable unit 1 is provided on the holder 3 so as to be capable of sliding in the axial direction, is capable of changing in position between a position in use and a stored position which is behind the position in use, and the movable unit 1 is fixed to the position in use so as to be releasable. The holder 3 includes a protecting cylinder 26 which stores only the front portion including a blade point 6A of the cannula 6 in the interior thereof when the movable unit is positioned at the stored position and is provided with the fixing wing 4, and a guide member 27 exposed upward for guiding the sliding movement of the movable unit 1.

5 Claims, 39 Drawing Sheets

INDWELLING NEEDLE WITH WINGS

TECHNICAL FIELD

The present invention relates to a winged indwelling needle to be punctured into an artery or the like and used for dialysis or the like.

RELATED ART

A winged indwelling needle to be punctured into an artery and used for dialysis or the like in the related art has a tubular protector fitted onto a cannula thereof after use. However, in the method described above, there is a possibility that a medical person punctures his/her finger which holds the protector with the cannula when fitting the protector, that is, a so-called erroneous puncture accident occurs and, consequently, the medical person is infected with AIDS or hepatitis.

As a winged indwelling needle which solves this problem, the following indwelling needle has been proposed (for example, see Patent Document 1). This indwelling needle includes "a cannula and a movable unit having a tubular hub with the front portion attached to the rear portion of the cannula", "a tube connected to the rear portion of the hub in communication with the cannula", "a holder having a protecting cylinder", and "a fixing wing provided on the protecting cylinder, having flexibility, and being adhered to a hand or an arm of a patient". The tube is connected to the hub outside the protecting cylinder, and the cannula, the hub and the holder are formed of a hard material.

The hub is provided on the holder so as to be slidable in the axial direction and the movable unit is capable of shifting between a position in use in which the front end portion of the hub and the cannula project toward the front from the protecting cylinder and a stored position behind the position in use in which the entire cannula is stored in the protecting cylinder, and the movable unit is fixed to the holder at the respective positions by being disengageably engaged with the holder at the respective positions.

In the related art, since the entire cannula is stored in the protecting cylinder when the movable unit is positioned at the stored position, the protecting cylinder and the hub need to have a sufficient length in the axial direction. Consequently, when the movable unit is positioned at the position in use, the axial distance from a joint portion between the hub and the tube to the fixing wing is significantly long.

In the meantime, when the indwelling needle in which the movable unit is fixed to the position in use is set on a patient, the fixing wing is adhered to the patient and the indwelling needle is fixed to the patient. However, when the tube is moved upward due to some reason (for example, a reason that the patient has moved or the tube has come into contact with something), the rear portion of the indwelling needle is apt to pivot upward about the fixing wing as a fulcrum, and the front portion of the indwelling needle is apt to pivot downward.

However, in the related art, since the distance from the joint portion between the hub and tube to the fixing wing in the axial direction is long, an external force of the movable unit to cause a pivotal movement is larger than a force to fix the indwelling needle by the fixing wing, and hence a blade point of the cannula pivots significantly downward, which may damage an artery or the like.

DISCLOSURE OF INVENTION

Problem to be Solved by the Invention

It is an object of the present invention to provide a winged indwelling needle which is capable of preventing erroneous puncture accidents by a cannula and has little possibility of damaging a blood vessel or the like by a blade point of the cannula being pivoted significantly downward even when a tube connected to a hub is moved upward in use.

Means for Solving the Problem

In order to achieve the above-described object, the present invention is characterized in that a winged indwelling needle includes A. a movable unit having a cannula and a cylindrical hub to be connected to the cannula with the rear portion of the cannula inserted into the front portion thereof, B. a tube which is connected to the rear portion of the hub and is brought into communication with the cannula, C. a holder, and D. a fixing wing having flexibility, the movable unit being provided on the holder so as to be capable of sliding in the axial direction, being capable of changing in position between a position in use and a stored position which is behind the position in use, and disengageably engaging the holder so as to be fixed to the holder when the movable unit is positioned at the position in use, wherein the holder includes (a) a protecting cylinder which is positioned at the front portion of the holder, allows the cannula to project forwardly from the front end thereof when the movable unit is positioned at the position in use and stores only the front portion including a blade point of the cannula in the interior thereof when the movable unit is positioned at the stored position, and is provided with the fixing wing, and (b) a guide member positioned at the rear of the holder for guiding the sliding movement of the movable unit and fixing the movable unit by engaging the movable unit when the movable unit is positioned at the stored position.

Furthermore, the guide member is formed into a plate shape having a planar shape on the upper and lower side, is exposed on the upper side, so that the tube is positioned above the guide member whereby the guide member allows the upward movement of the tube when the movable unit is positioned at the position in use.

Furthermore, the guide member is formed with a depressed portion for allowing the guide member to bend upward so that it may curve when a compression force in the axial direction is exerted.

Furthermore, the movable unit includes an operating member for operating the movable unit secured to the hub, the operating member includes A. a pivoting arm being capable of pivotal movement and disengageably engaging the holder through the pivotal movement when the movable unit is positioned at the position in use, and B. a slider which is slidable in the axial direction with respect to the guide member, and the guide member is provided at the rear portion thereof with engaging means for engaging the slider to fix the movable unit in the stored position.

Furthermore, the holder includes A. a substantially ring shaped lock portion connected to the rear end portion of the protecting cylinder and the front end portion of the guide member and disengageably engaged with the pivoting arm, and B. a cover extending rearward from the lock portion for covering the axial midsection of the cannula when the movable unit is positioned at the stored position.

Furthermore, the movable unit includes A. the operating member for operating the movable unit secured to the hub, and B. a fixing member which is provided on the hub and the guide member so as to be capable of sliding in the axial direction and is engaged with the hub and the guide member so as not to come apart therefrom when the movable unit is moved to the stored position, thereby fixing the movable unit at the stored position, and the operating member includes the pivoting arm which is capable of the pivotal movement and is disengageably engaged with the holder through the pivotal movement when the movable unit is positioned at the position in use.

Furthermore, the fixing member has a hollow shape, the hub and the guide member are inserted into the interior of the fixing member, the fixing member is formed with an engaging projection and an engaging recess in the interior thereof, the hub is formed with an engaging groove with which the engaging projection is engageable so as not to come apart therefrom, and the guide member is formed at the rear portion thereof with an engaging claw which is engageable with the engaging recess so as not to come apart therefrom.

BEST MODE FOR CARRYING OUT THE INVENTION

EXAMPLE 1

Showing an Embodiment

Figure 1:
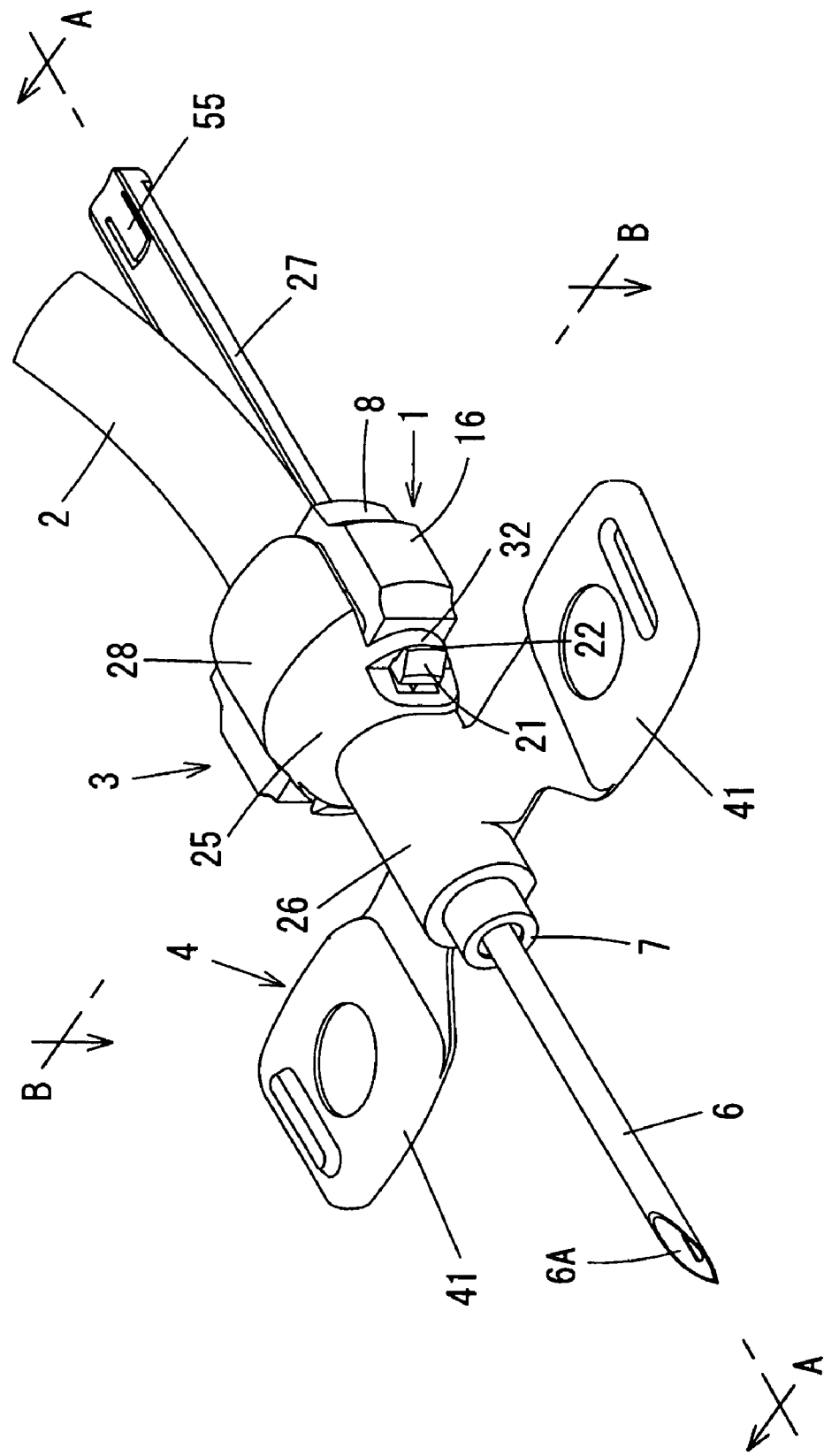
FIG. 1 is a perspective view illustrating Example 1 showing an embodiment of the present invention.
Figure 2:
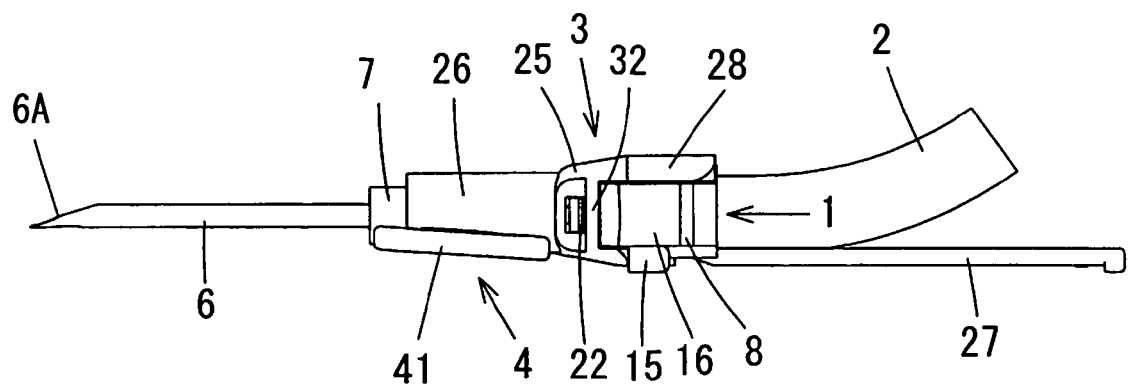
FIG. 2 is a side view of FIG. 1.
Figure 3:
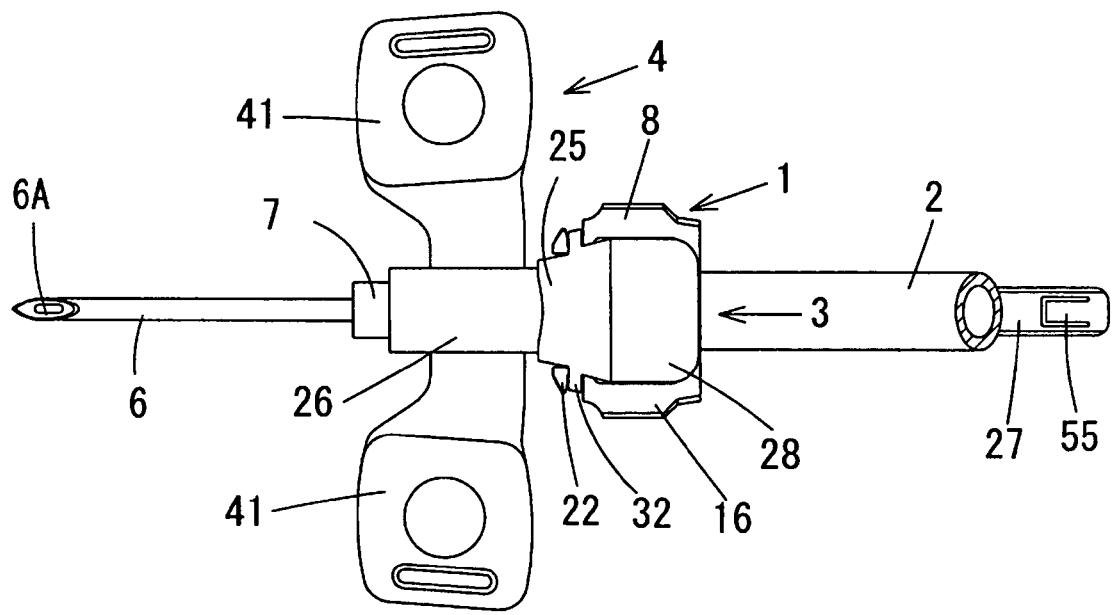
FIG. 3 is a plan view of FIG. 1.
Figure 4:
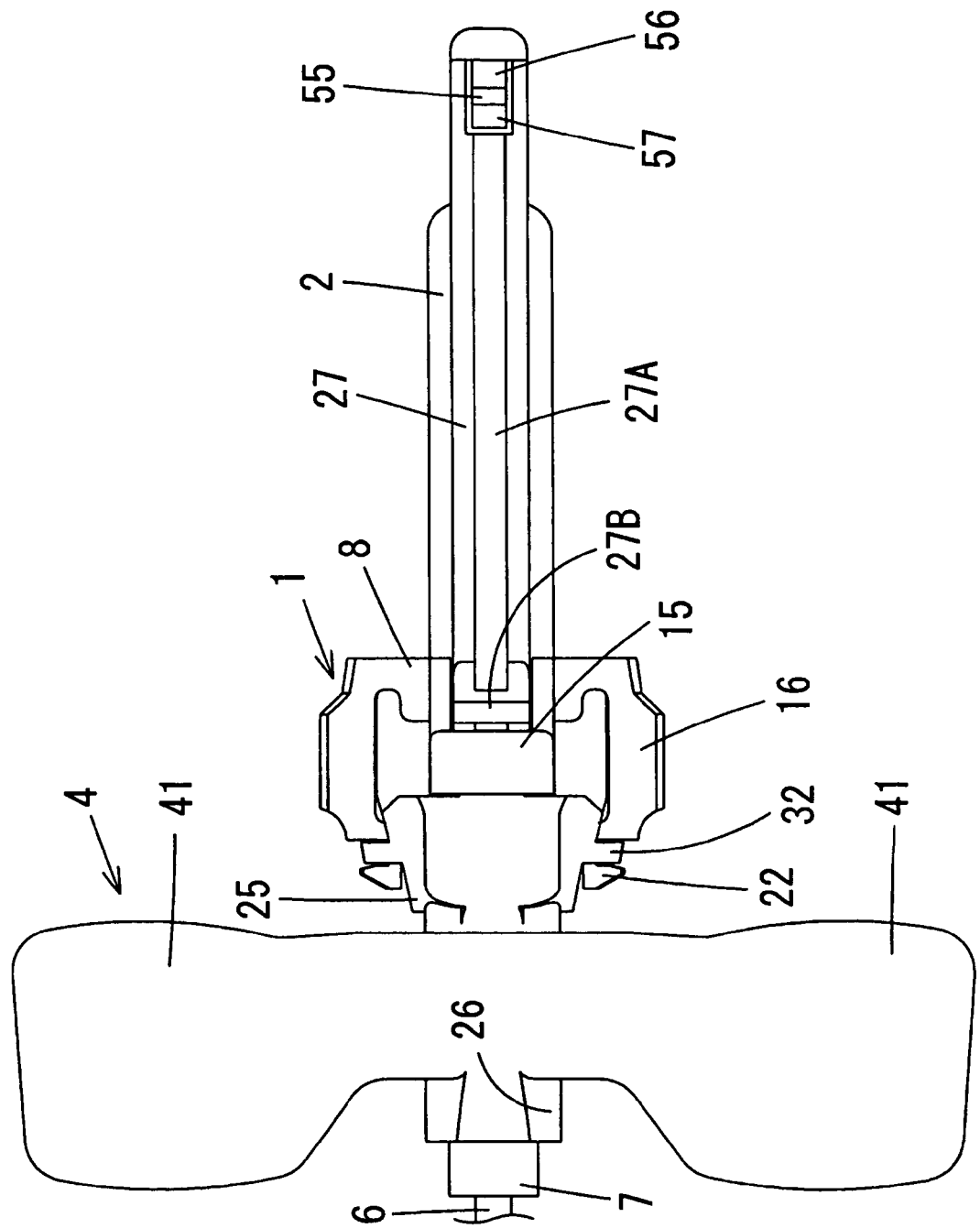
FIG. 4 is a bottom view of FIG. 1.
Figure 5:
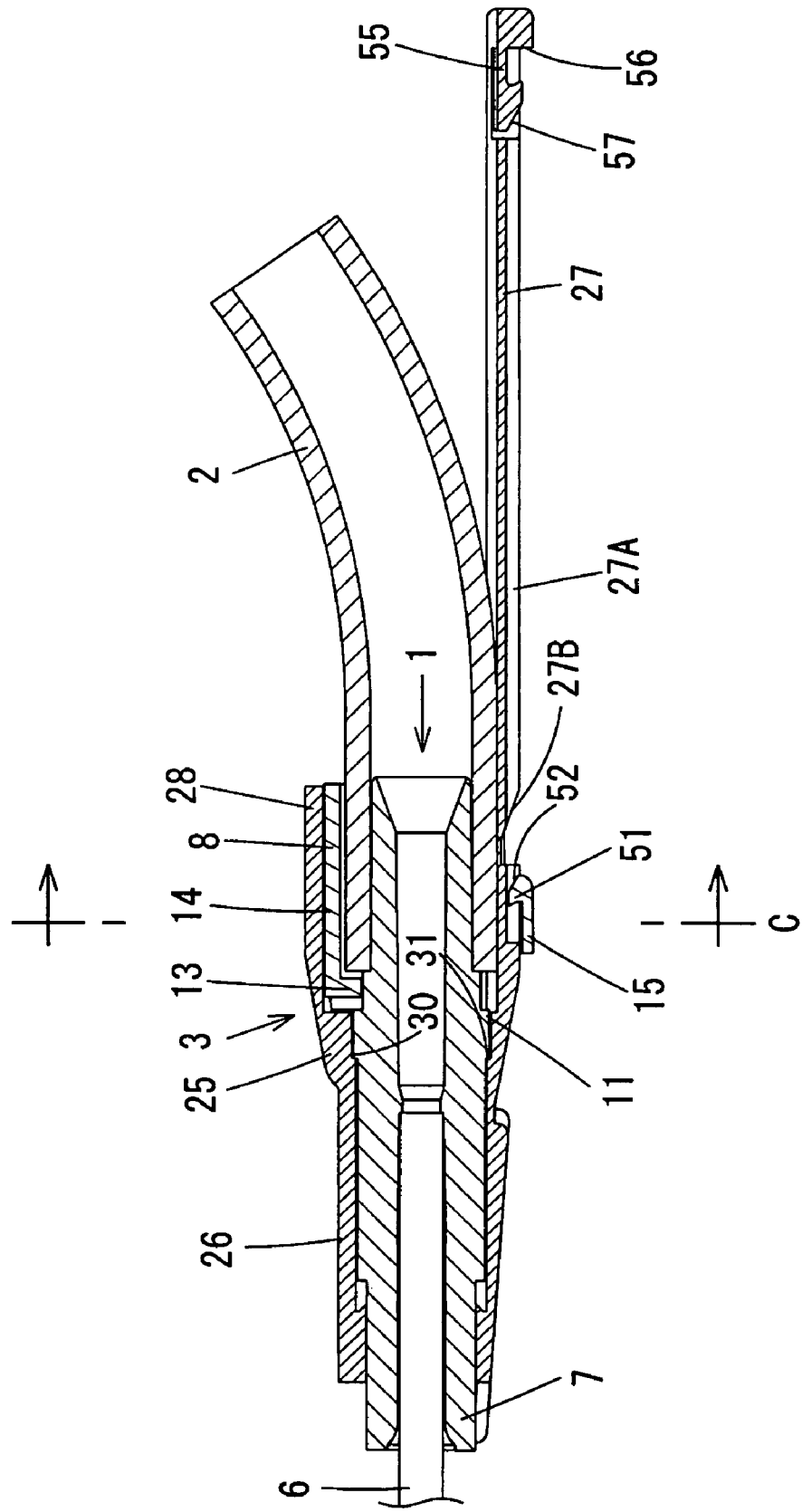
FIG. 5 is a cross-sectional view taken along the line A-A in FIG. 1.
Figure 6:
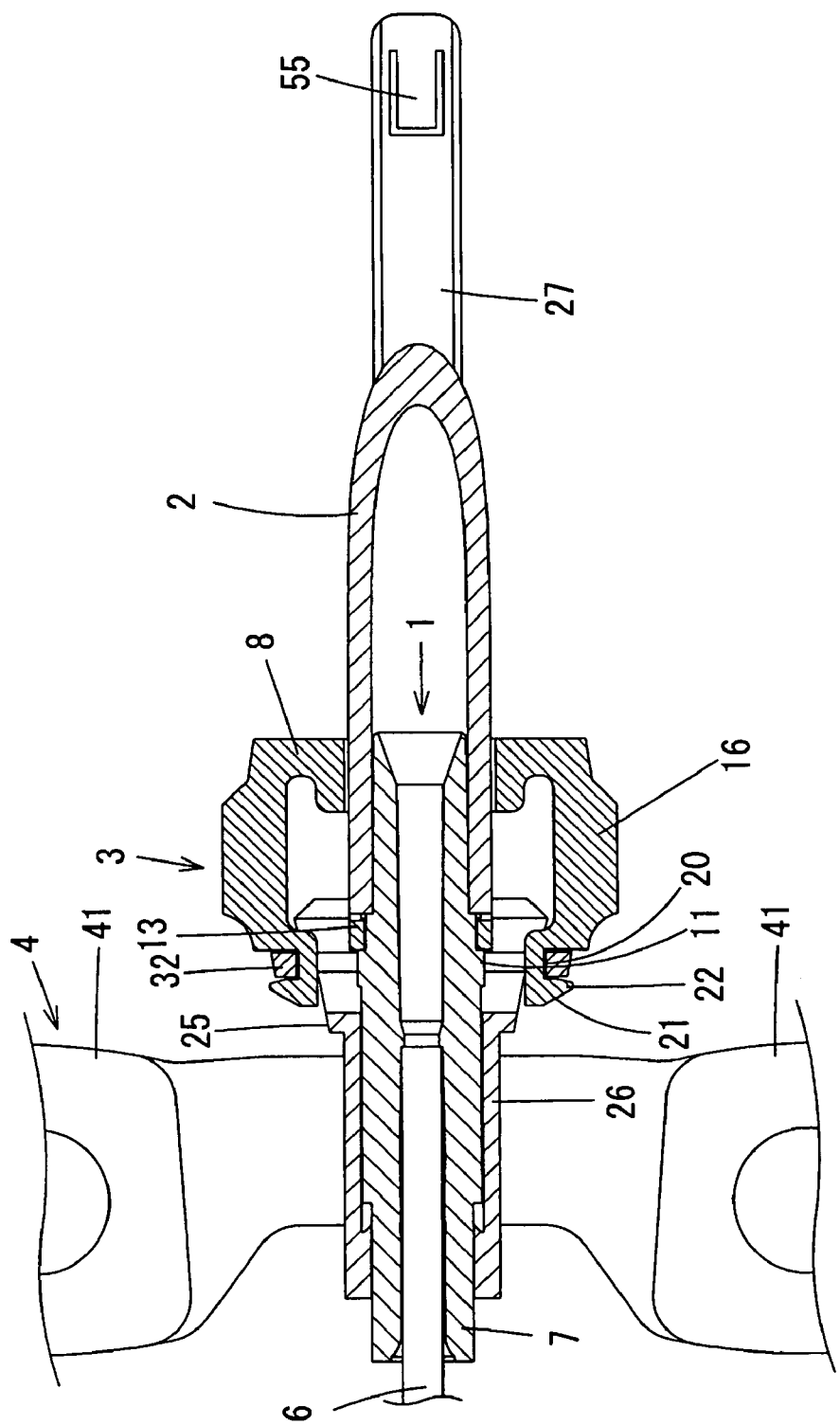
FIG. 6 is a cross-sectional view taken along the line B-B in FIG. 1.
Figure 7:
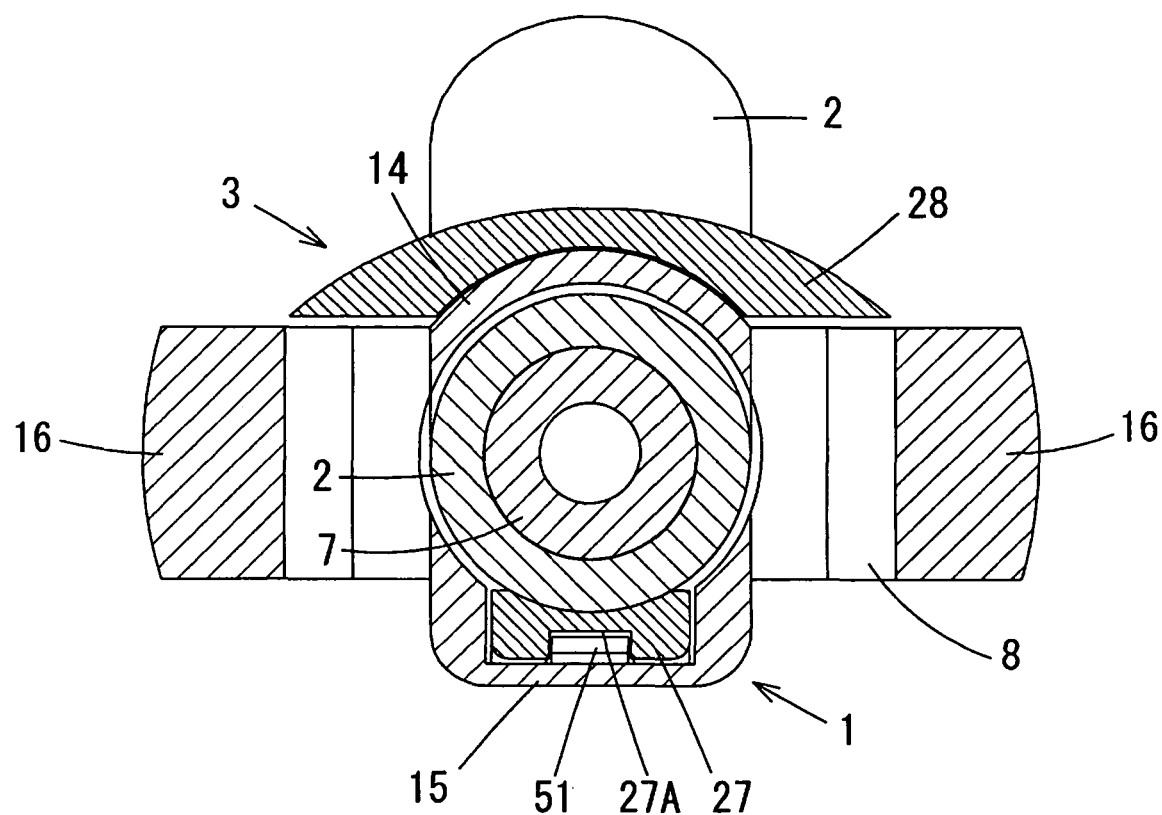
FIG. 7 is a cross-sectional view taken along the line C-C in FIG. 5.
Figure 8:
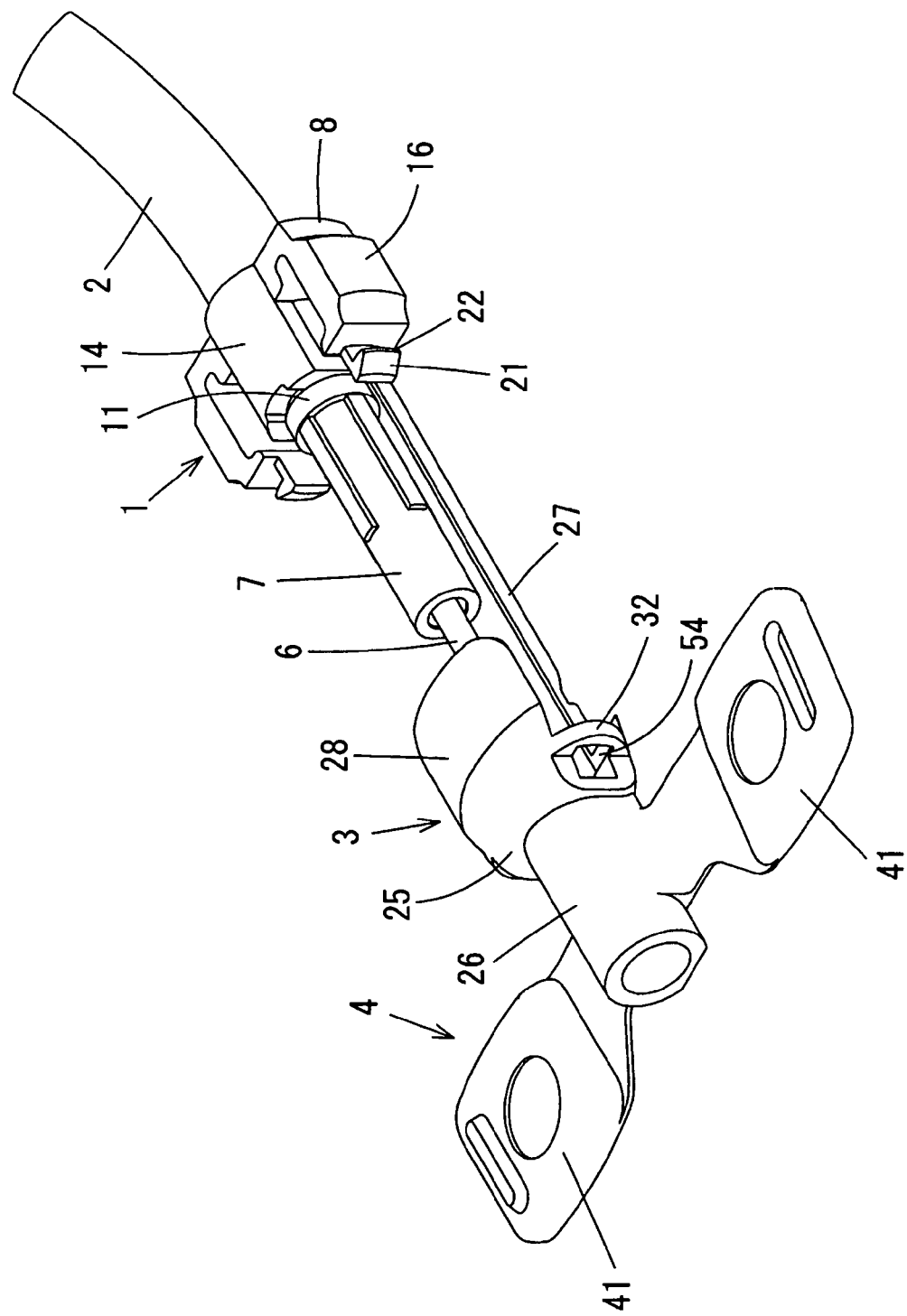
FIG. 8 is a perspective view illustrating a state in which a movable unit of FIG. 1 is positioned at a stored position.
Figure 9:
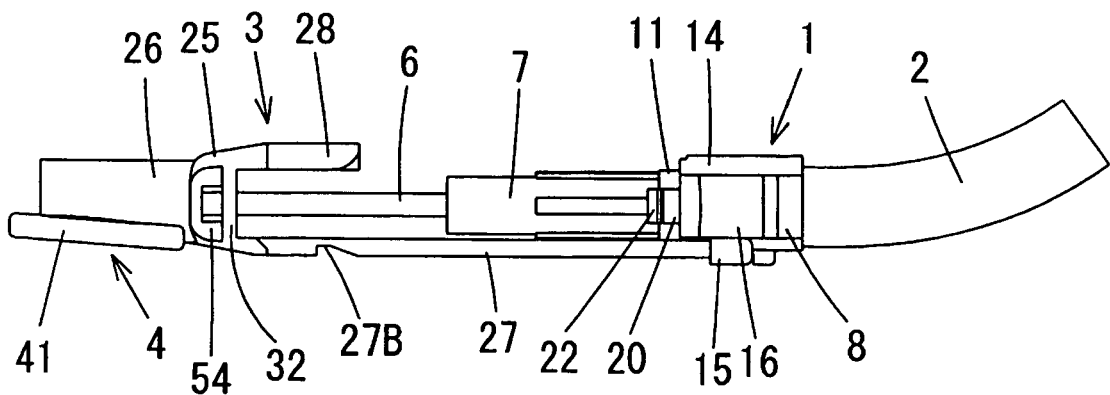
FIG. 9 is a side view of FIG. 8.
Figure 10:
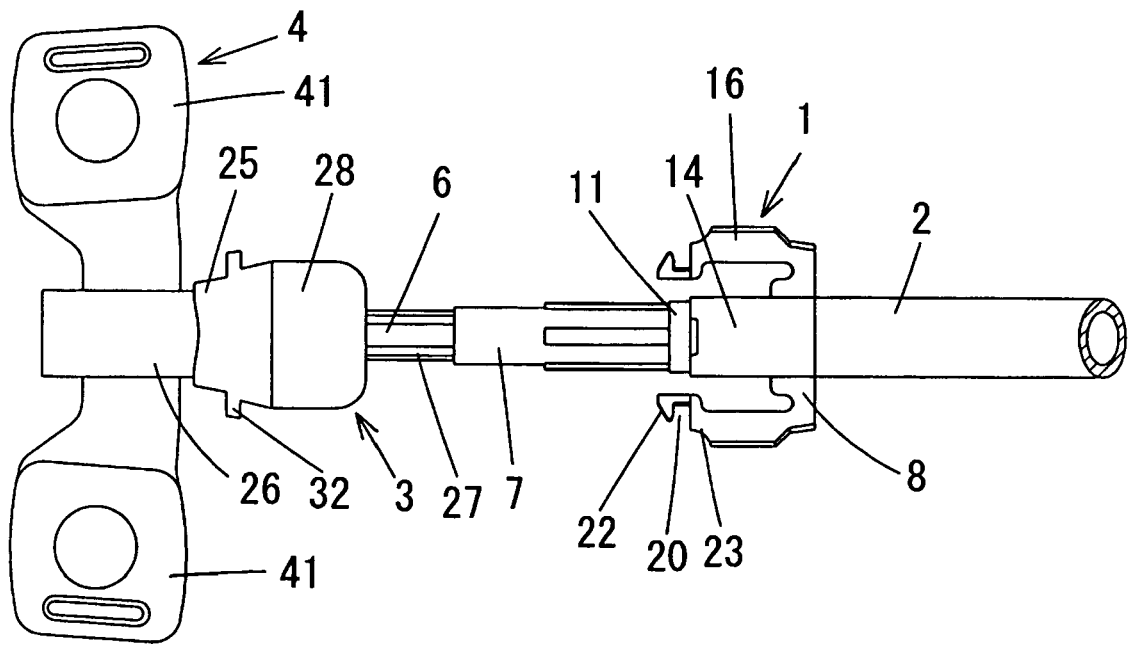
FIG. 10 is a plan view of FIG. 8.
Figure 11:
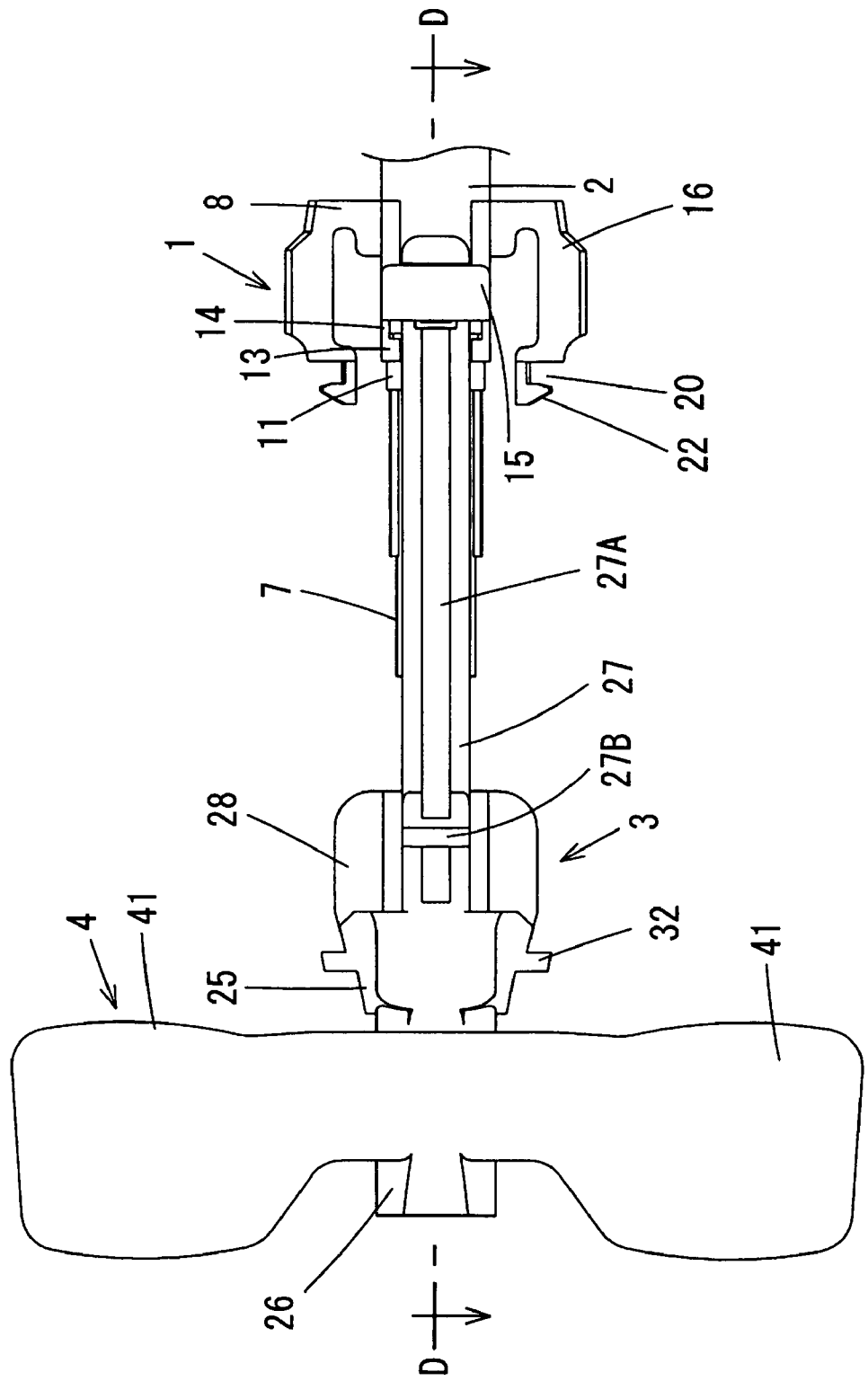
FIG. 11 is a bottom view of FIG. 8.
Figure 12:
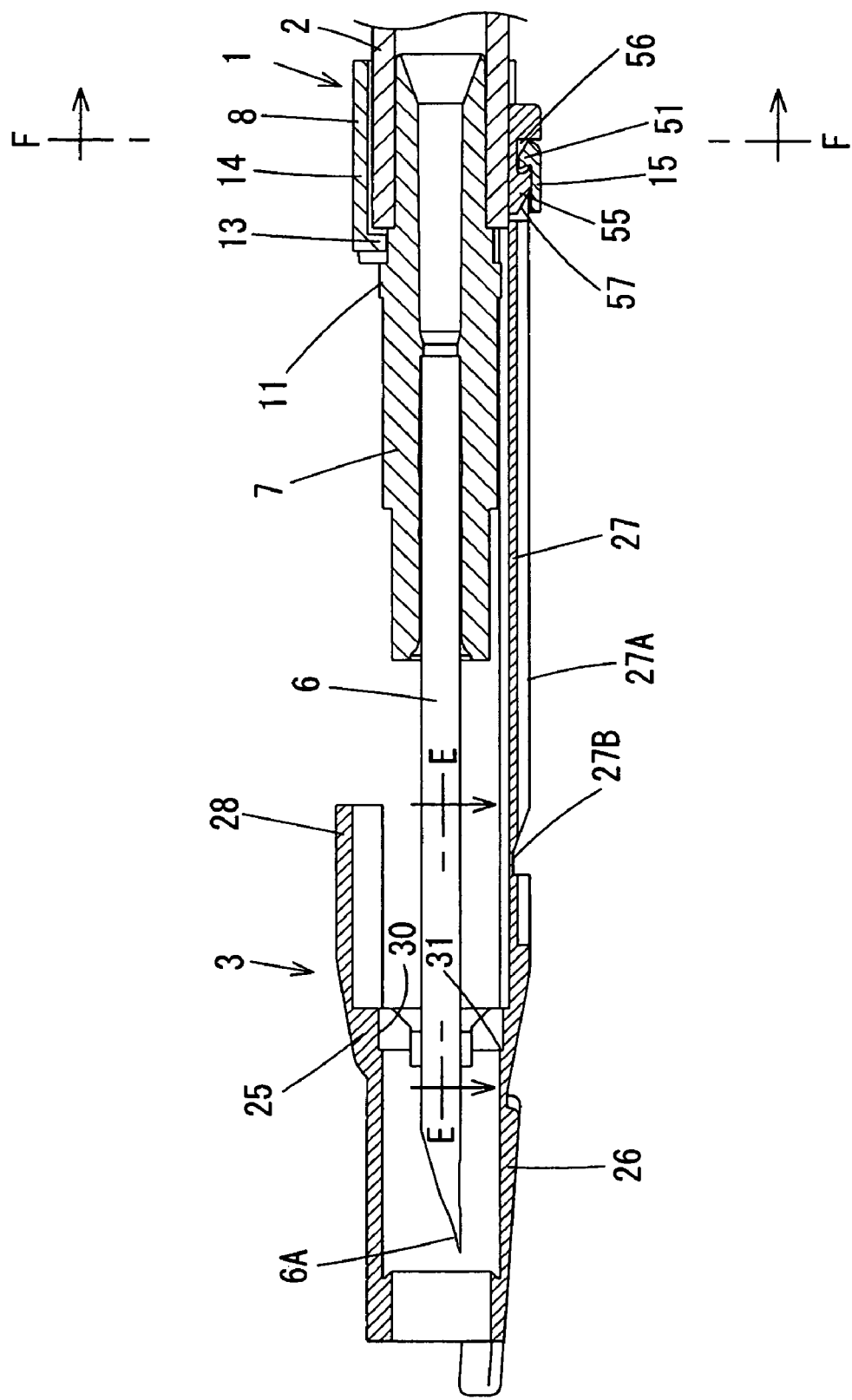
FIG. 12 is a cross-sectional view taken along the line D-D in FIG. 11.
Figure 13:
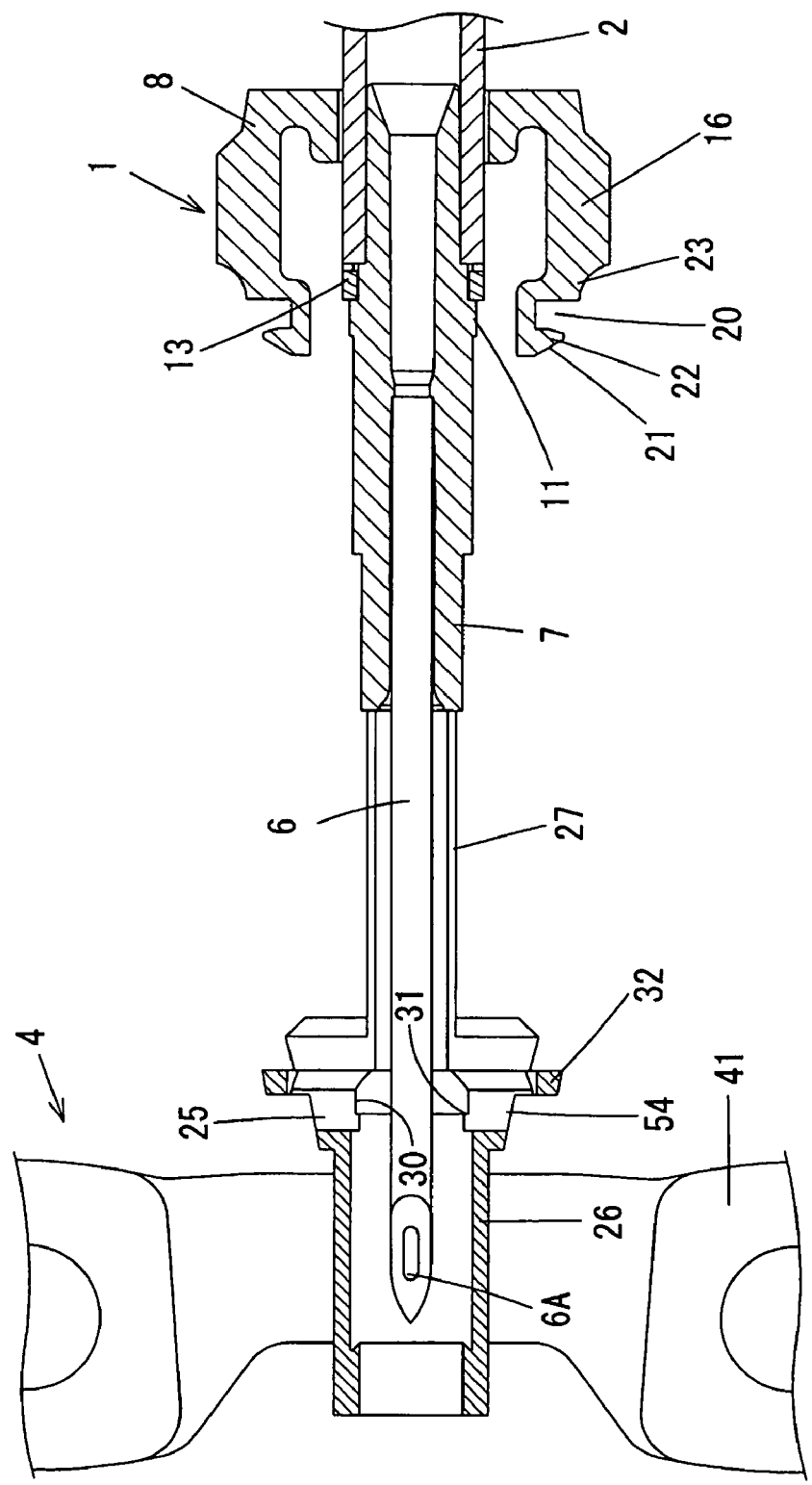
FIG. 13 is a cross-sectional view taken along the line E-E in FIG. 12.
Figure 14:
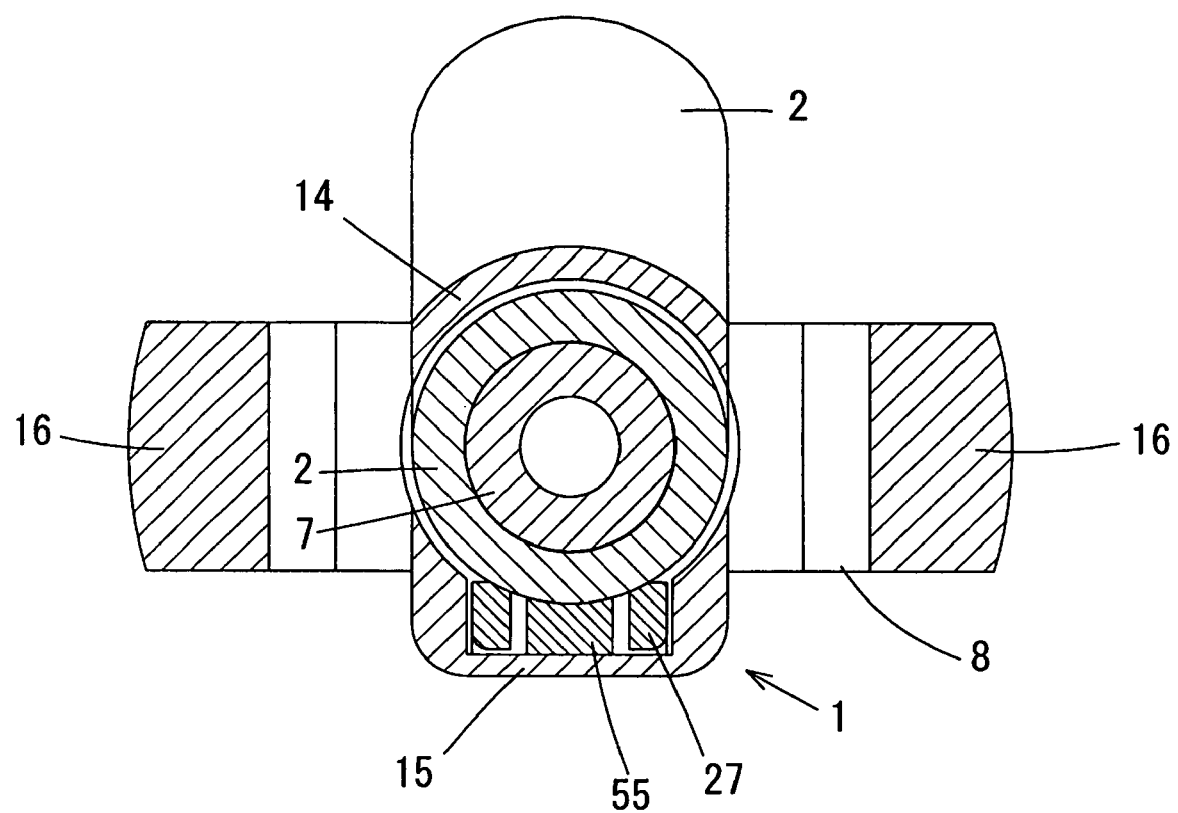
FIG. 14 is a cross-sectional view taken along the line F-F in FIG. 12.
Figure 15:
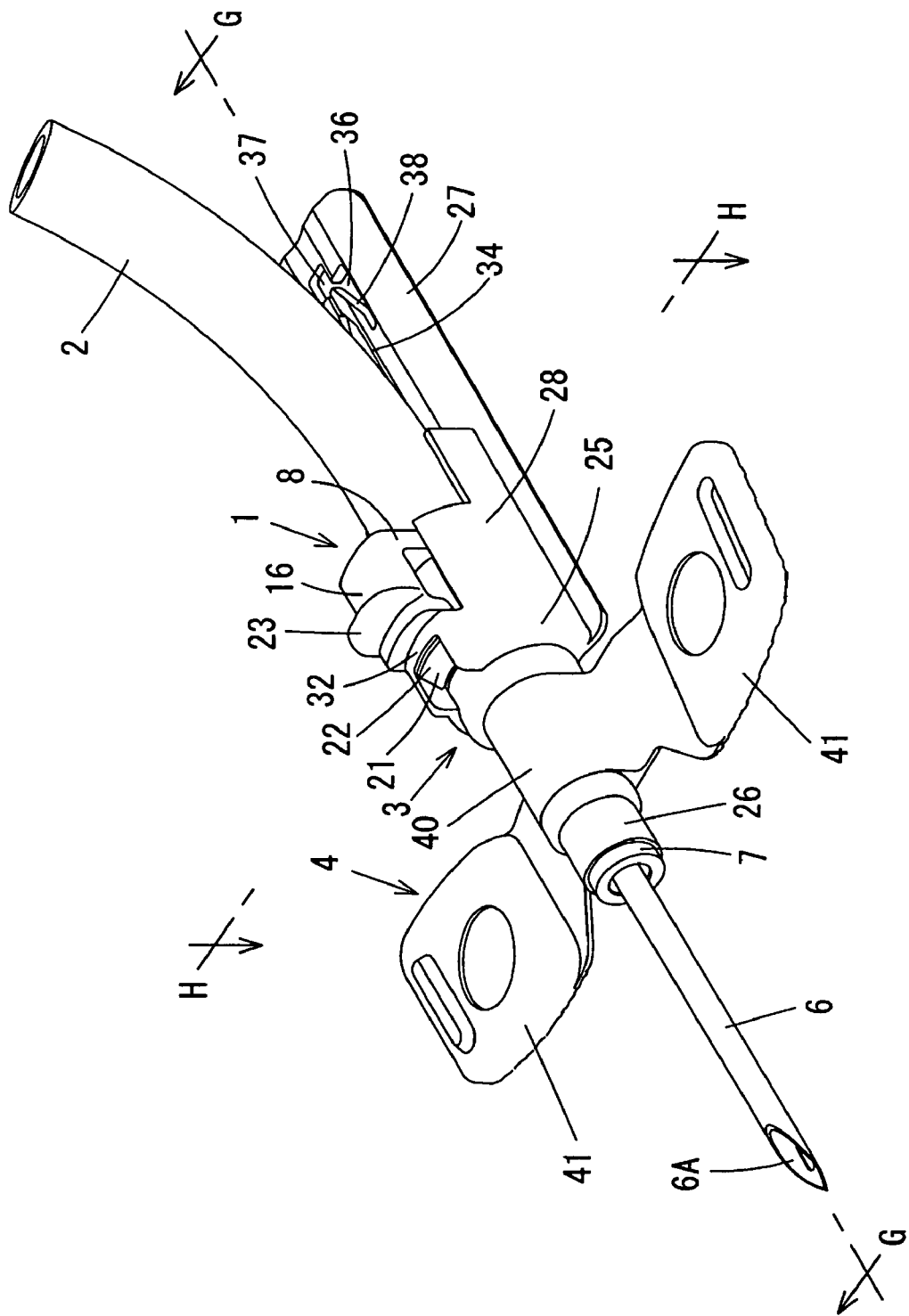
FIG. 15 is a perspective view illustrating Example 2 showing another embodiment of the present invention.
Figure 16:
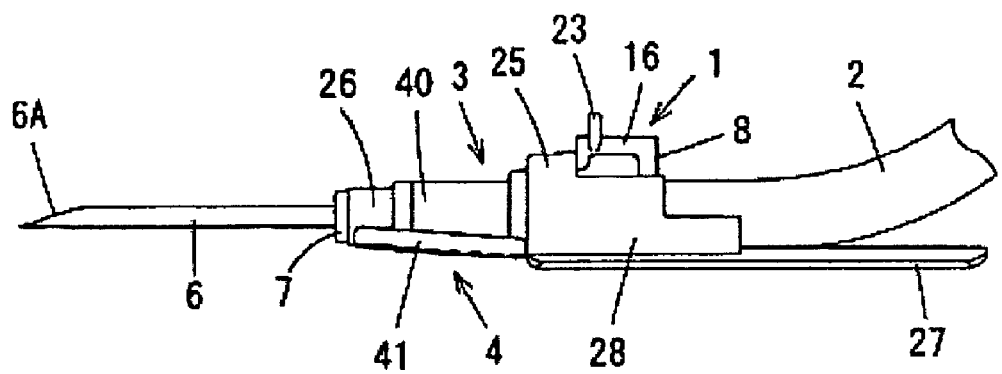
FIG. 16 is a side view of FIG. 15.
Figure 17:
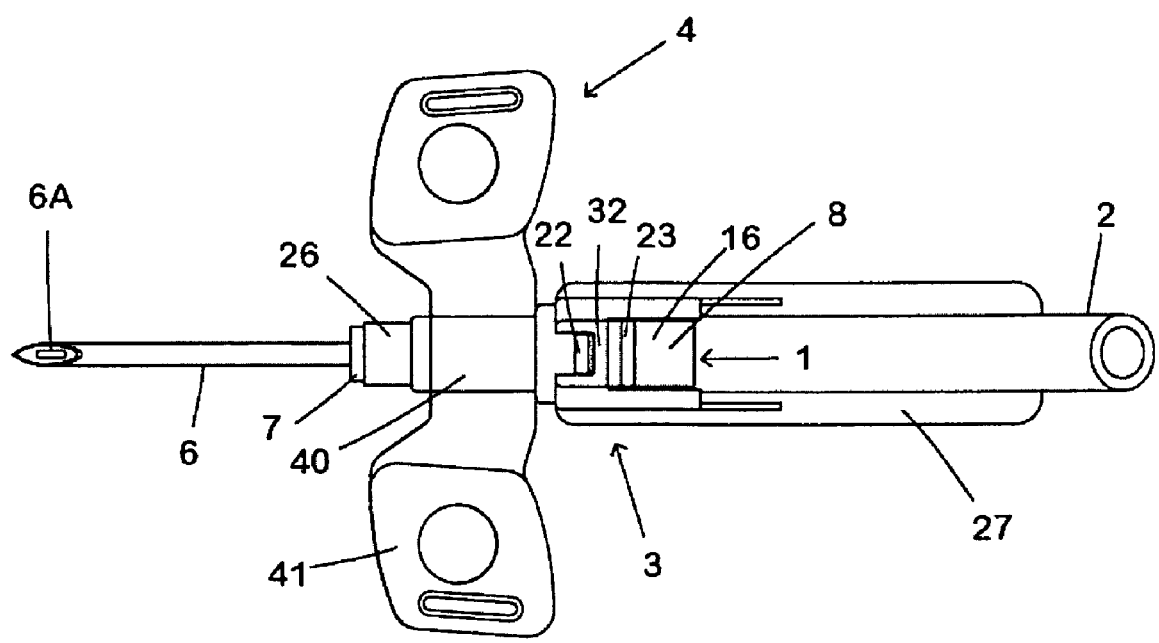
FIG. 17 is a plan view of FIG. 15.

Referring now to FIG. 1 to FIG. 14, Example 1 showing an embodiment of the present invention will be described. A winged indwelling needle includes a movable unit 1, a tube 2, a holder 3 and a fixing wing 4.

The movable unit 1 is provided on the holder 3 so as to be slidable (movable) in the axial direction, and includes a cannula 6, a hub 7 and an operating member 8.

The cannula 6 is an elongated tube and the front end portion thereof is formed into a pointed blade point 6A. The cannula 6 is integrally formed of a hard material having resiliency such as stainless steel (preferably, SUS304).

The hub 7 is formed into a cylindrical shape opening at both ends in the axial direction, and the rear portion of the cannula 6 is inserted and fitted to the front portion thereof. The axial midsection of the hub 7 is a large-diameter portion 11 having a larger diameter than other portions. The hub 7 is integrally formed of a hard material having resiliency, for example, a thermoplastic resin such as vinyl chloride, ABS resin, polycarbonate, polypropylene, polyester, and polyethylene.

The operating member 8 is used for operating the movable unit 1, and includes a fitting portion 13, a rearwardly protruding portion 14, a slider (sliding member, moving member) 15 and a pair of left and right pivoting arms 16, and is formed integrally of a hard material having resiliency like the hub 7. These members may be formed separately and assembled. The fitting portion 13 has a ring shape of which the lower side is cut out (removed), is fitted onto the rear portion of the hub 7 from the rear, and comes into abutment with the large-diameter portion 11 of the hub 7 in terms of the axial direction. The rearwardly protruding portion 14 extends rearward from both left and right side portions of the fitting portion 13. The rearwardly protruding portion 14 opens on the lower side, and includes windows on both side portions thereof. The slider 15 connects the lower end portions of the left and right side portions of the rearwardly protruding portion 14, includes an engaging projection 51 protruding upward from the rear end portion thereof, and the rear surface of the engaging projection 51 is an inclined surface 52 inclining toward the front. The respective pivoting arms 16 extend outward and frontward from the rear end portion of the rearwardly protruding portion 14. The respective pivoting arms 16 are pivotable in the widthwise direction through resilient deformation, and the front portion thereof is formed with an inwardly recessed engaged portion 20 and a projection 22 formed so as to be continuously projected therefrom and having inclined surfaces 21 which are sloped inwardly toward the front.

The tube 2 is fitted onto the rear portion of the hub 7, is connected to the hub 7 with adhesive agent or the like, and communicates with the cannula 6 via the hub 7. At this time, the connected end of the tube 2 clamps at least part of the fitting portion 13 of the operating member 8 in cooperation with the large-diameter portion 11 of the hub 7, so that the operating member 8 is prevented from coming off from the hub 7. The tube 2 is preferably formed of a material being translucent and having flexibility and is integrally formed, for example, of the same material as the hub 7.

The holder 3 is provided with the movable unit 1 so as to be movable in the axial direction, and is capable of being shifted in position between a position in use shown in FIG. 1 to FIG. 7 and a stored position which is behind the position in use shown in FIG. 8 to FIG. 14. The holder 3 includes a lock portion 25, a protecting cylinder 26, a guide member 27 and a cover 28, and is integrally formed of a hard material like the hub 7.

The lock portion 25 is formed substantially in a ring shape, and the inner surface includes a large-diameter portion 30 which is larger in diameter than the front end portion at the axial midsection thereof. A stepped surface 31 having a planar shape at the rear is formed on the inner surface at a boundary between the large-diameter portion 30 and the front end portion. When the movable unit 1 is positioned at the position in use, the large-diameter portion 11 of the hub 7 is fitted into the large-diameter portion 30, and is brought into abutment with the stepped surface 31 in terms of the axial direction. The cover 28 protruding upward in a curved shape extends rearward from the lock portion 25, and covers the axial midsection of the cannula 6 when the movable unit 1 is positioned at the stored position. The lock portion 25 is also provided with engaging portions 32 extending in the vertical direction on the left and right sides thereof, and insertion ports 54 penetrated therethrough in the widthwise direction at the front side of the engaging portions 32 so that the projections 22 of the pivoting arms 16 are detachably inserted therein to fix the movable unit 1 at the position in use.

The protecting cylinder 26 is projected forward from the front end portion of the lock portion 25. When the movable unit 1 is positioned at the position in use, the front portion of the hub 7 is inserted in the interior of the protecting cylinder 26 so as to be slidable (movable) in the axial direction, so that the front end portion of the hub 7 and the cannula 6 project forwardly of the protecting cylinder 26. When the movable unit 1 is positioned at the stored position, only the front portion of the cannula 6 including the blade point 6A is stored in the interior of the protecting cylinder 26. Accordingly, the axial lengths of protecting cylinder 26 and the hub 7 are reduced, so that the distance from the joint portion between the hub 7 and the tube 2 to the fixing wing 4 in terms of the axial direction is reduced when the movable unit is positioned at the position in use.

The guide member 27 is used for guiding the movable unit 1 in the axial direction, and formed into an axially elongated plate shape having a planar shape on the upper and lower side. The slider 15 is arranged below the guide member 27 so as to be slidable in the axial direction. A guide groove 27A is formed on the lower surface of the guide member 27 so as to be recessed toward the upper side. An angular C-shaped cut is formed at the rear end portion of the guide member 27, so that an engaging piece 55 which is pivotable in the vertical direction and serves as engaging means is provided. An engaging recess 56 with which the engaging projection 51 engages so as not to come apart therefrom when the movable unit 1 reaches the stored position is formed on the lower surface of the rear portion of the engaging piece 55 so as to be recessed toward the upper side, and the lower surface of the front portion of the engaging piece 55, that is, the front portion of the engaging recess 56 on the lower surface is formed with an inclined surface 57 which is inclined upward toward the front. The guide member 27 is formed to protrude rearward from the lower end portion of the rear portion of the lock portion 25. The front portion of the guide member 27 is formed with a depressed portion (hinge, notched portion) 27B depressed from the side of the lower surface. Accordingly, when a compression force in the axial direction is exerted to the guide member 27, the guide member 27 is bent into an upwardly curved protruding shape. The rear surface of the inner portion of the depressed portion 27B is inclined upward toward the front.

The fixing wing 4 is integrally formed with the protecting cylinder 26, and includes a pair of left and right wings 41 formed so as to extend outward from the protecting cylinder 26. The fixing wing 4 is integrally formed of the same material as the hub 7, and has flexibility and resiliency. The wings 41 are adhered to an arm or a hand of a patient.

In this configuration, when the winged indwelling needle is in use, the movable unit 1 is positioned at the position in use as shown in FIG. 1 to FIG. 7, in which the front end portion of the hub 7 and the cannula 6 project forward from the protecting cylinder 26. The projections 22 of the operating member 8 of the movable unit 1 engage with the engaging portions 32 of the lock portion 25 of the holder 3, and the movable unit 1 is fixed to the position in use.

In order to set the winged indwelling needle to the hand or the arm of the patient, the cannula 6 is punctured into an artery in the hand or the arm of the patient, and the fixing wing 4 is adhered to the hand or the arm of the patient, so that the winged indwelling needle is fixed to the patient.

When the tube 2 is moved upward or to the left or right by some cause, the movement of the tube 2 is transmitted to the movable unit 1. For example, when the rear portion of the movable unit 1 is pivoted upward, the front portion of the movable unit 1, that is, the cannula 6 is pivoted downward. This pivotal movement occurs with the fixing wing 4, which is fixed to the patient, as a fulcrum. Therefore the pivotal movement which is transmitted to the cannula 6 increases with an increase in distance from the fixing wing 4 to a portion where the movement of the tube 2 is not impaired. Since total length of a holder for storing a cannula in a winged indwelling needle in the related art is long, and a tube is connected to the terminal of a hub having substantially the same length as the holder, the axial distance from the fixing wing to the portion where the movement of the tube is not impaired, that is, to a joint portion between the tube and the hub, is large.

However, since the winged indwelling needle in the present invention has the guide member 27 behind the holder 3, the tube 2 is exposed to the upward and lateral directions, and the hub 7 has substantially the same length as the total length of the protecting cylinder 26, the lock portion 25 and the cover 28 which are provided forwardly of the holder 3. Therefore, the axial distance from the fixing wing 4 to the joint portion between the tube 2 and the hub 7 is dramatically reduced, and hence the pivotal movement of the cannula 6 caused by the movement of the tube is reduced, so that the possibility of damage of an artery or the like caused by the blade point 6A of the cannula 6 is reduced.

When removing the indwelling needle from the patient, the pivoting arms 16 of the operating member 8 of the movable unit 1 are pivoted inwardly to separate the projection 22 of the pivoting arms 16 from the engaging portion 32 of the lock portion 25 of the holder 3, and then the movable unit 1 is slid rearward, so that only the front portion including the blade point 6A of the cannula 6 is stored in the protecting cylinder 26. Accordingly, such an event that a finger or the like of a medical person is punctured by the cannula 6, i.e., a so-called erroneous puncture accident is prevented, so that the possibility that the medical person is infected by AIDS or hepatitis is eliminated.

In the above-described case, since the cover 28 on the upper side covers the axial midsection of the cannula 6, even when blood or the like of the patient is attached to the axial midsection of the cannula 6, the blood is prevented from attaching to medical person.

When the slider 15 reaches the rear portion of the guide member 27 during the sliding movement of the movable unit 1 described above, the inclined surface 52 of the engaging projection 51 of the slider 15 comes into abutment with the inclined surface 57 of the engaging piece 55 of the guide member 27 to pivot the engaging piece 55 upward, and brings the engaging projection 51 into engagement with the engaging recess 56 of the engaging piece 55 so as not to come apart therefrom and restores the engaging piece 55 to the original position by a resilient restoration force, so that the movable unit 1 is fixed to the stored position.

In the meantime, in this case, if the depressed portion 27B is formed on the guide member 27, when a rearward external force is exerted on the protecting cylinder 26 and a compression force in the axial direction is exerted on the guide member 27, the guide member 27 is bent to an upwardly curved shape. Therefore, the blade point 6A of the cannula 6 is directed toward the front and obliquely downward, so that the possibility of puncturing medical person is reduced.

EXAMPLE 2

Showing Another Embodiment

FIG. 15 to FIG. 28 illustrate Example 2 showing another embodiment of the present invention and different points from Example 1 are mainly described below. The operating member 8 of the movable unit 1 includes the rearwardly protruding portions 14 protruding rearward from both the left and right side portions of the fitting portion 13. The slider 15 protrudes downward from the lower end portion of the fitting portion 13 into an inverted T-shape and includes a sliding portion 18 on the upper side and a retaining portion 19 having a wider width than the sliding portion 18. The pivoting arm 16 is a single member and protrudes upward and then forward from the rear end portions of the both rearwardly protruding portions 14 so as to be pivotable in the vertical direction through resilient deformation. An engaged portion 20 and a projection 22 are formed in the front end of the pivoting arm 16 in order toward the front. The engaged portion 20 is recessed downwardly. The projection 22 projects upward and has an inclined surface 21 which is inclined toward the rear. The pivoting arm 16 includes an operating portion 23 extending upright at the axial midsection of the pivoting arm 16 for pressing the pivoting arm 16 downward.

The lock portion 25 of the holder 3 is provided with an engaging portion 32 extending laterally in the widthwise direction at the upper end portion thereof, so that the inclined surface 21 of the projection 22 of the pivoting arm 16 of the operating member 8 comes into abutment with the engaging portion 32 when the movable unit 1 is being positioned at the position in use, the pivoting arm 16 is pivoted downward and the engaging portion 32 disengageably engages relatively with the engaged portion 20 of the pivoting arm 16 from above, so that the movable unit 1 is fixed to the position in use.

The widthwise center portion of the guide member 27 is at a level higher than the both end portions, and is in a floating state. The guide member 27 is formed at the widthwise center thereof with a guide groove 34 penetrating therethrough in the vertical direction and extending in the axial direction, so that the sliding portion 18 of the slider 15 of the operating member 8 is fitted to the guide groove 34 and is guided in the axial direction, and the slider 15 is prevented from coming apart from the guide groove 34 by the retaining portion 19 of the slider 15. The retaining portion 19 is in a state of being stored on the side of the lower surface of the guide member 27. The guide groove 34 is formed at the axial midsection thereof with an insertion port 35 having a slightly larger size than the retaining portion 19 of the slider 15, so that the slider 15 is inserted into the insertion port 35 from above when inserting the sliding portion 18 of the slider 15 into the guide groove 34. The guide groove 34 is formed at the rear portion thereof with engaging means including a wide portion 36 being wider than other portions, an engaging groove 37 having the same width as other portions and being continued toward the rear, and a pair of left and right pivotal strips 38 being pivotable toward the outside and protruding rearward from left and right sides of the front edge portion of the wide portion 36. The rear portions of the respective pivotal strips 38 are inclined toward the widthwise center of the wide portion 36 as it goes to the rear, and the rear end portions of the both pivotal strips 38 are opposed to each other with a slight gap interposed therebetween. When the movable unit 1 is positioned at the position in use, the slider 15 is positioned at the front end portion of the guide groove 34, and when the movable unit 1 is positioned at the stored position, the slider 15 is positioned at the engaging groove 37 and the slider 15 is prevented from coming apart from the engaging groove 37 by the pivotal strips 38.

The cover 28 is provided so as to extend upright on both the left and right sides of the front portion of the guide member 27, and the front end portion thereof is connected to the lock portion 25 so as to be formed into an outwardly curved protruding shape, so that the axial midsection of the cannula 6 is covered when the movable unit 1 is positioned at the stored position.

Figure 18:
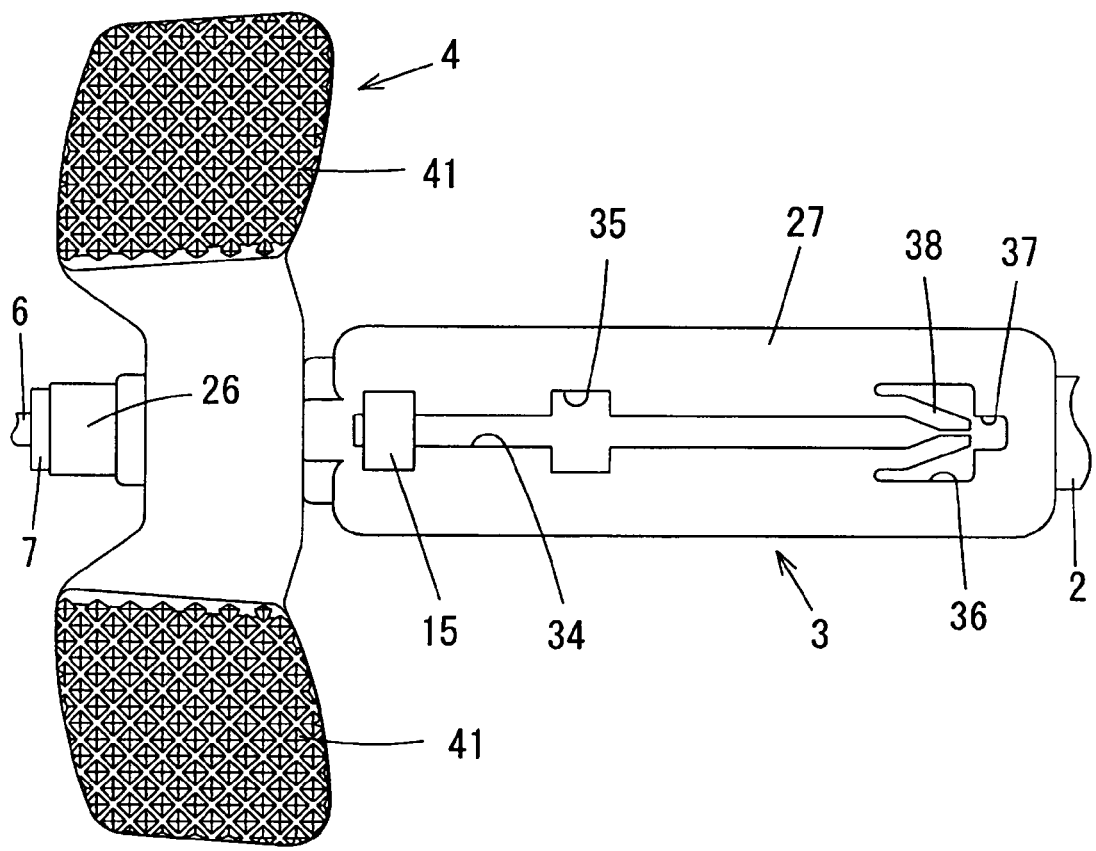
FIG. 18 is a bottom view of FIG. 15.
Figure 19:
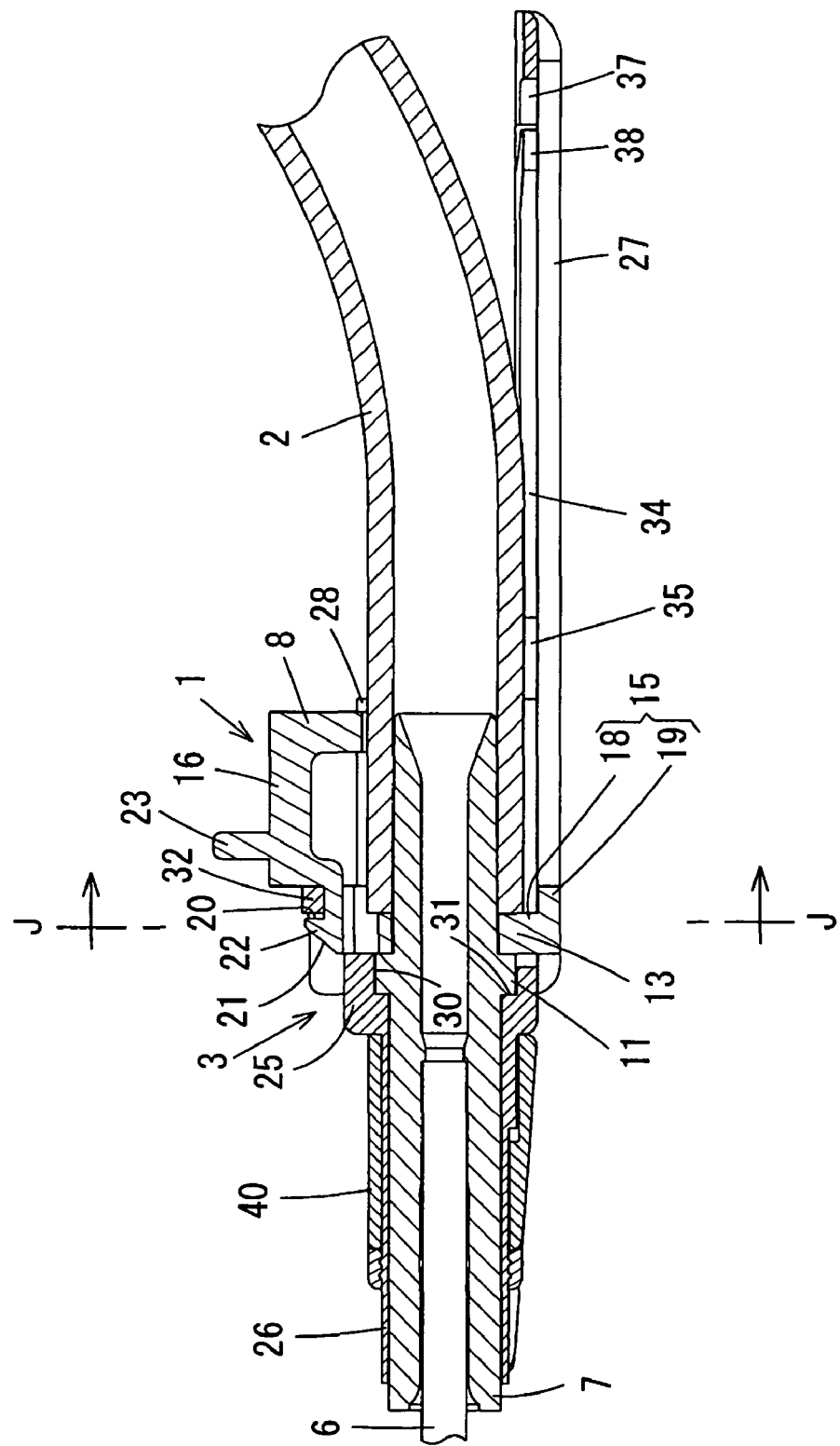
FIG. 19 is a cross-sectional view taken along the line G-G in FIG. 15.
Figure 20:
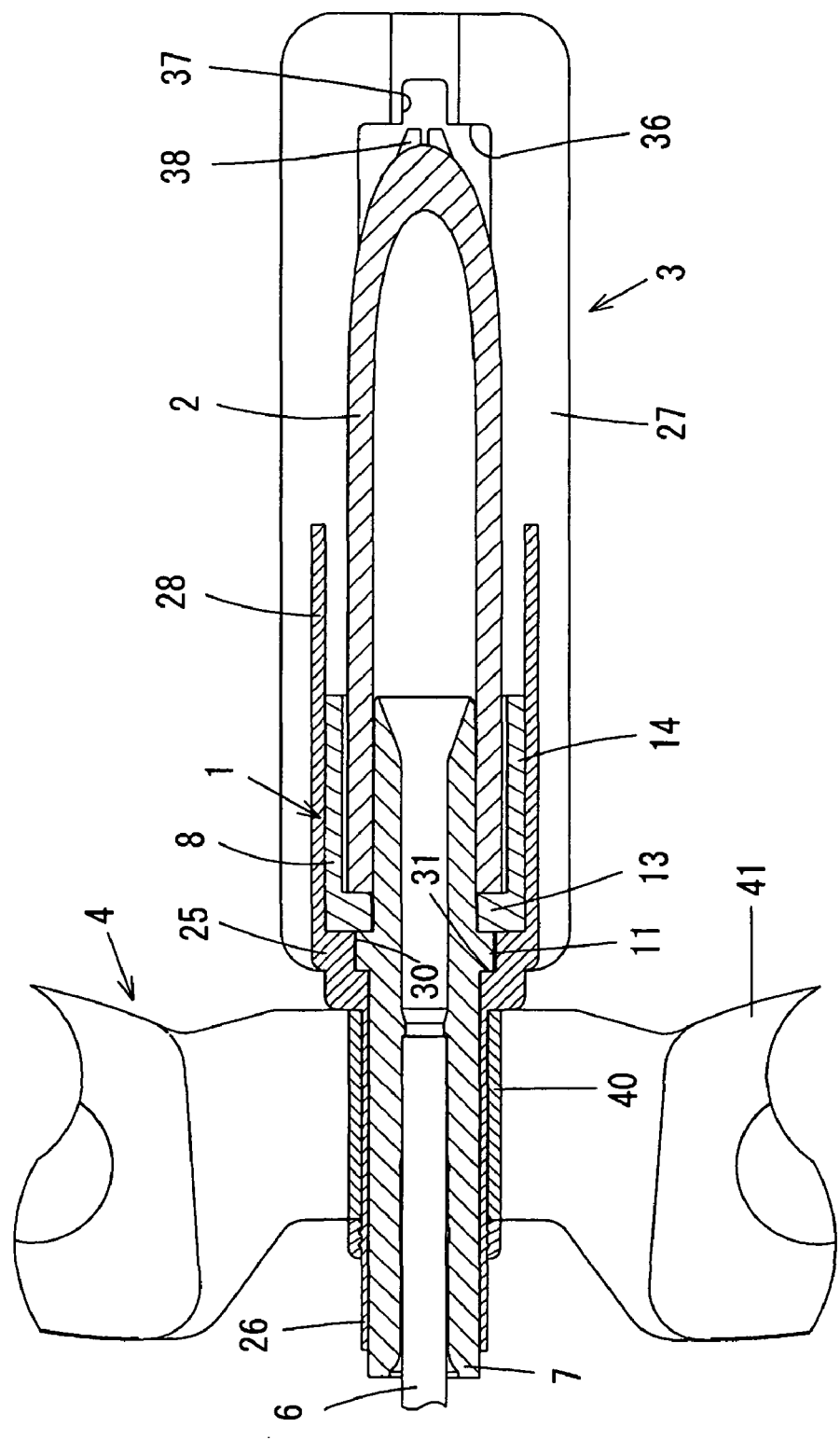
FIG. 20 is a cross-sectional view taken along the line H-H in FIG. 15.
Figure 21:
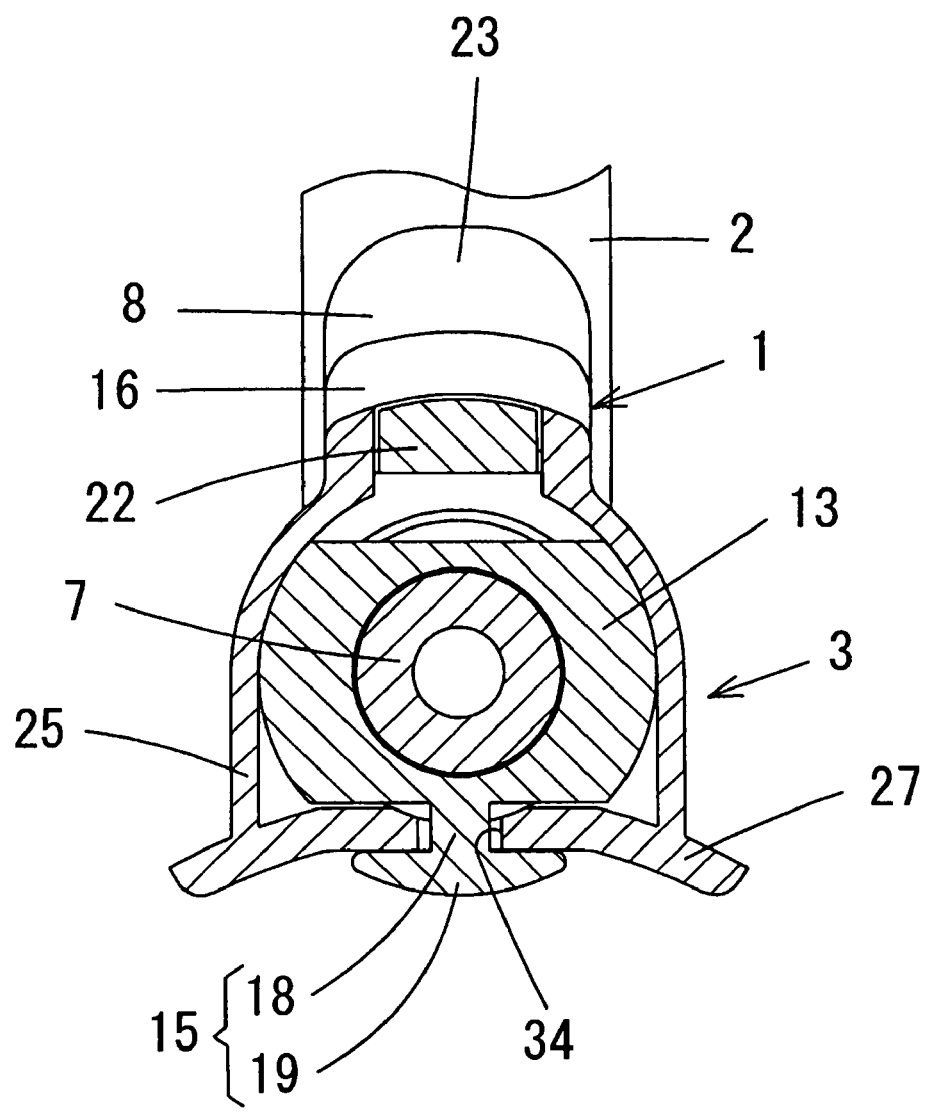
FIG. 21 is a cross-sectional view taken along the line J-J in FIG. 19.
Figure 22:
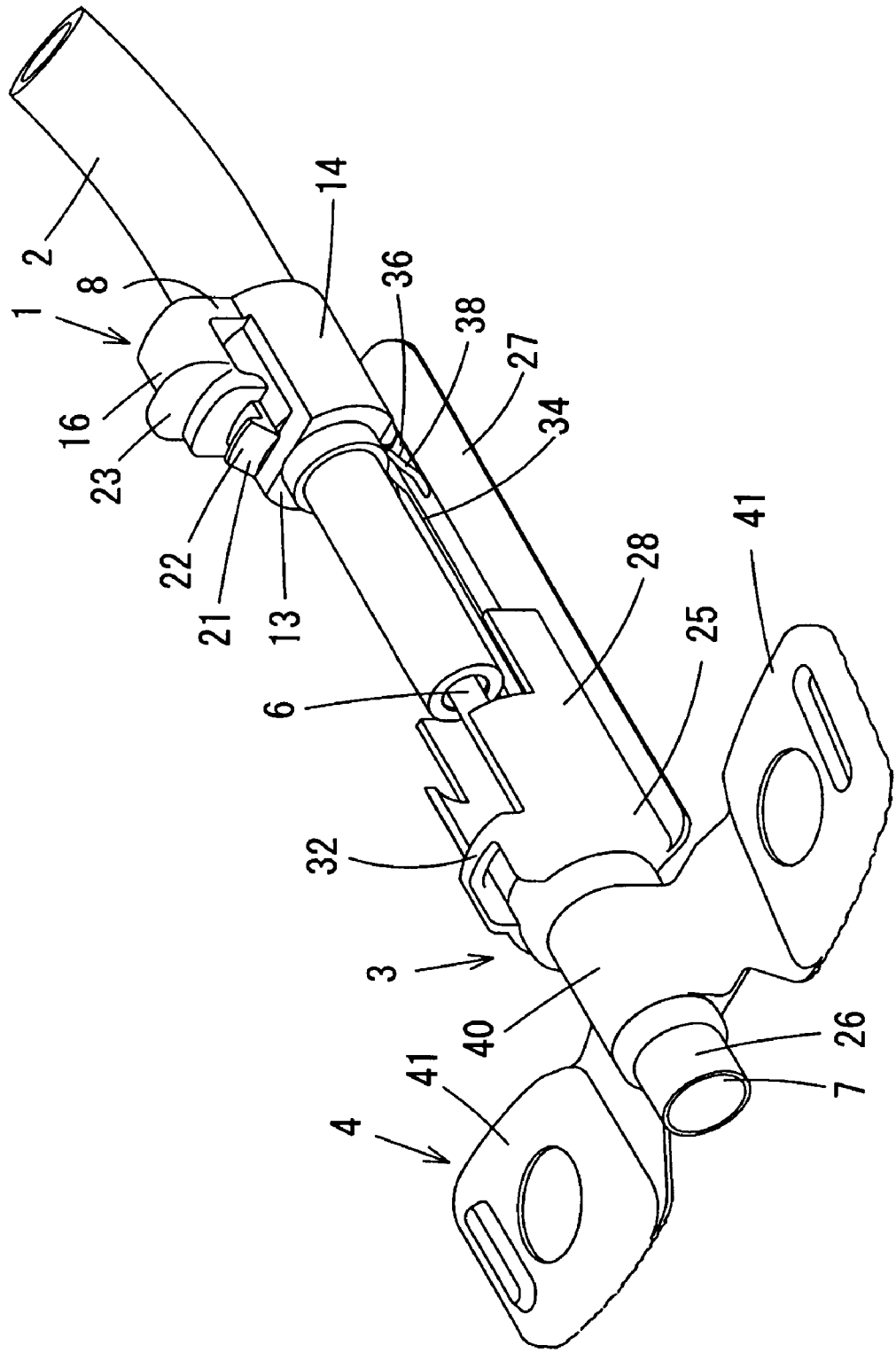
FIG. 22 is a perspective view illustrating a state in which the movable unit in FIG. 15 is positioned at the stored position.
Figure 23:
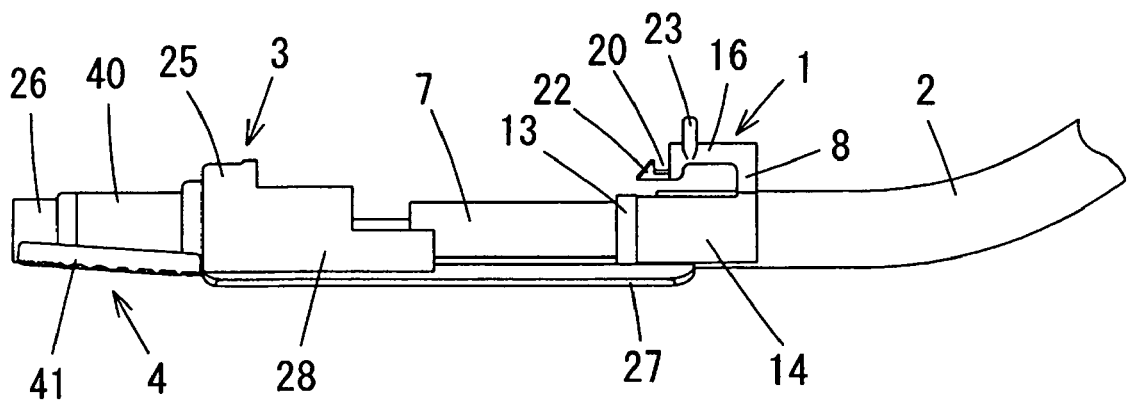
FIG. 23 is a side view of FIG. 22.
Figure 24:
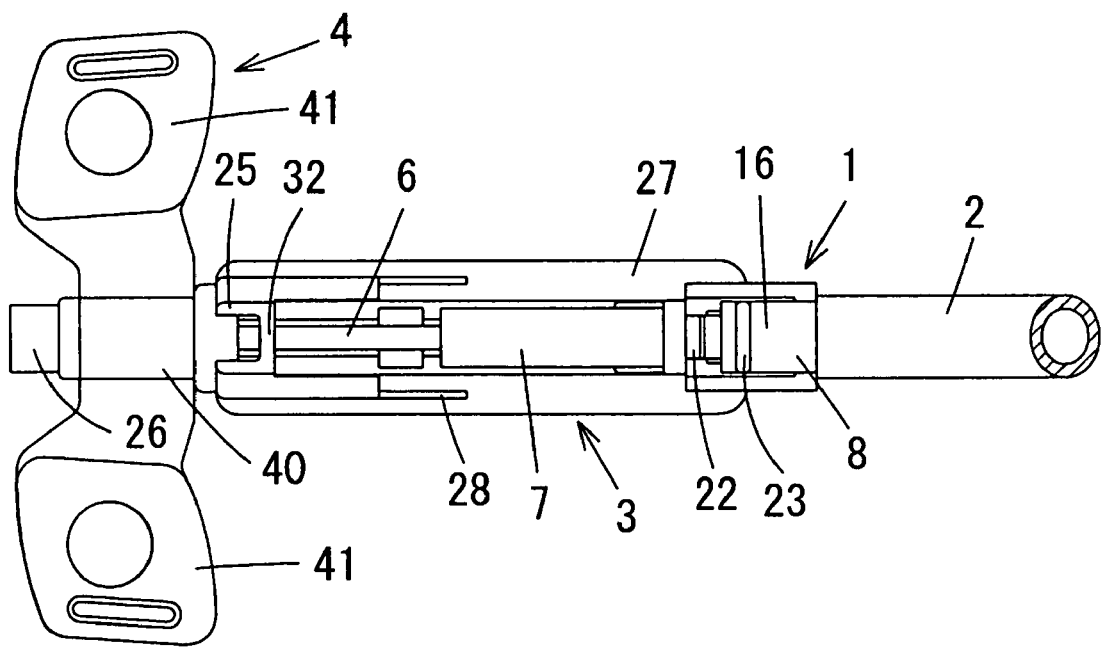
FIG. 24 is a plan view of FIG. 22.
Figure 25:
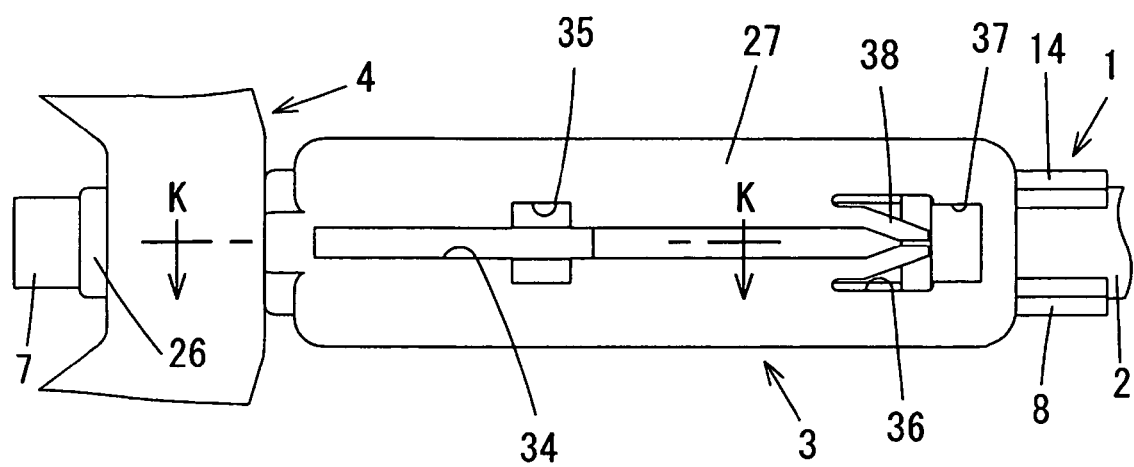
FIG. 25 is a bottom view of FIG. 22.
Figure 26:
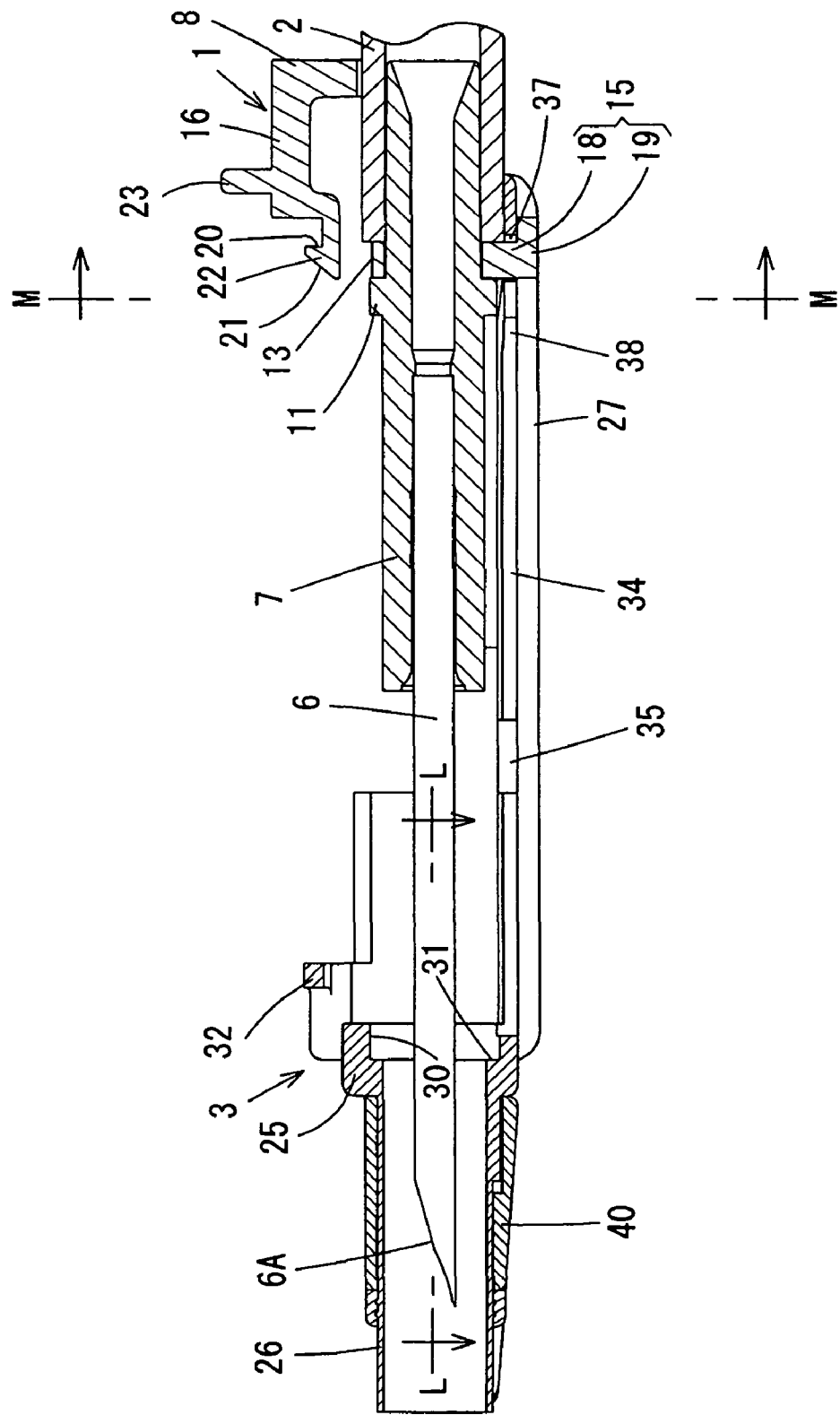
FIG. 26 is a cross-sectional view taken along the line K-K in FIG. 25.
Figure 27:
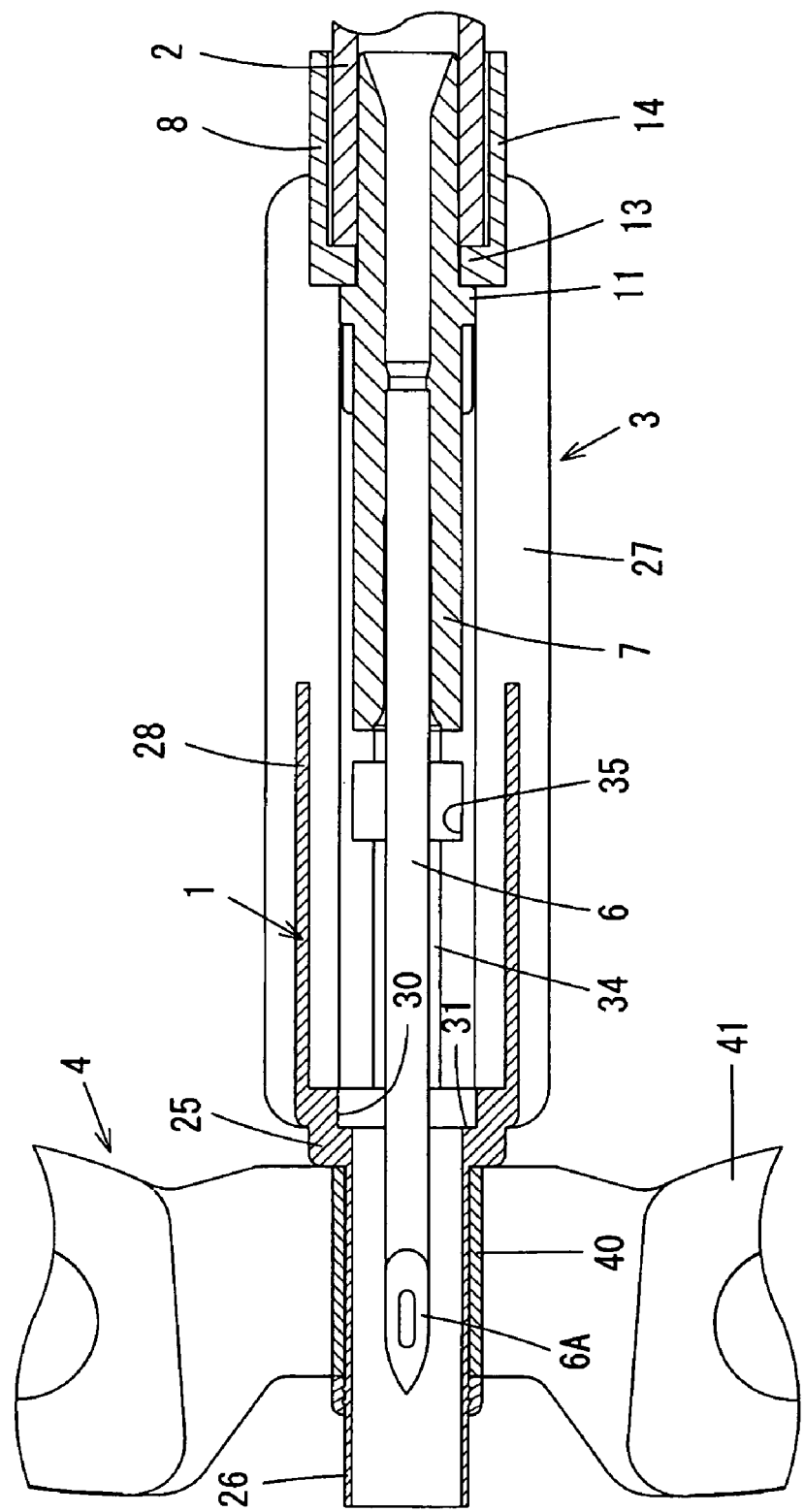
FIG. 27 is a cross-sectional view taken along the line L-L in FIG. 26.
Figure 28:
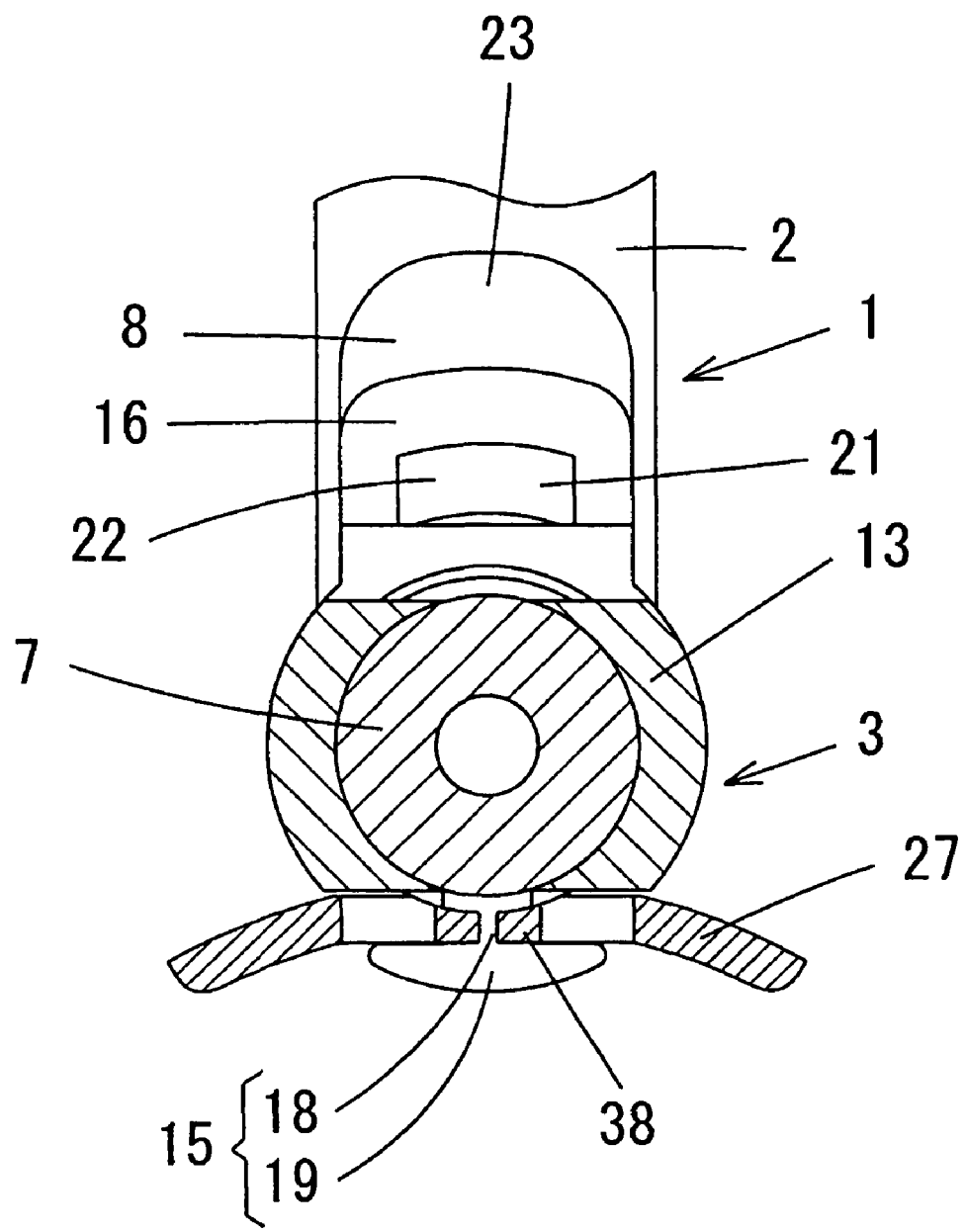
FIG. 28 is a cross-sectional view taken along the line M-M in FIG. 26.
Figure 29:
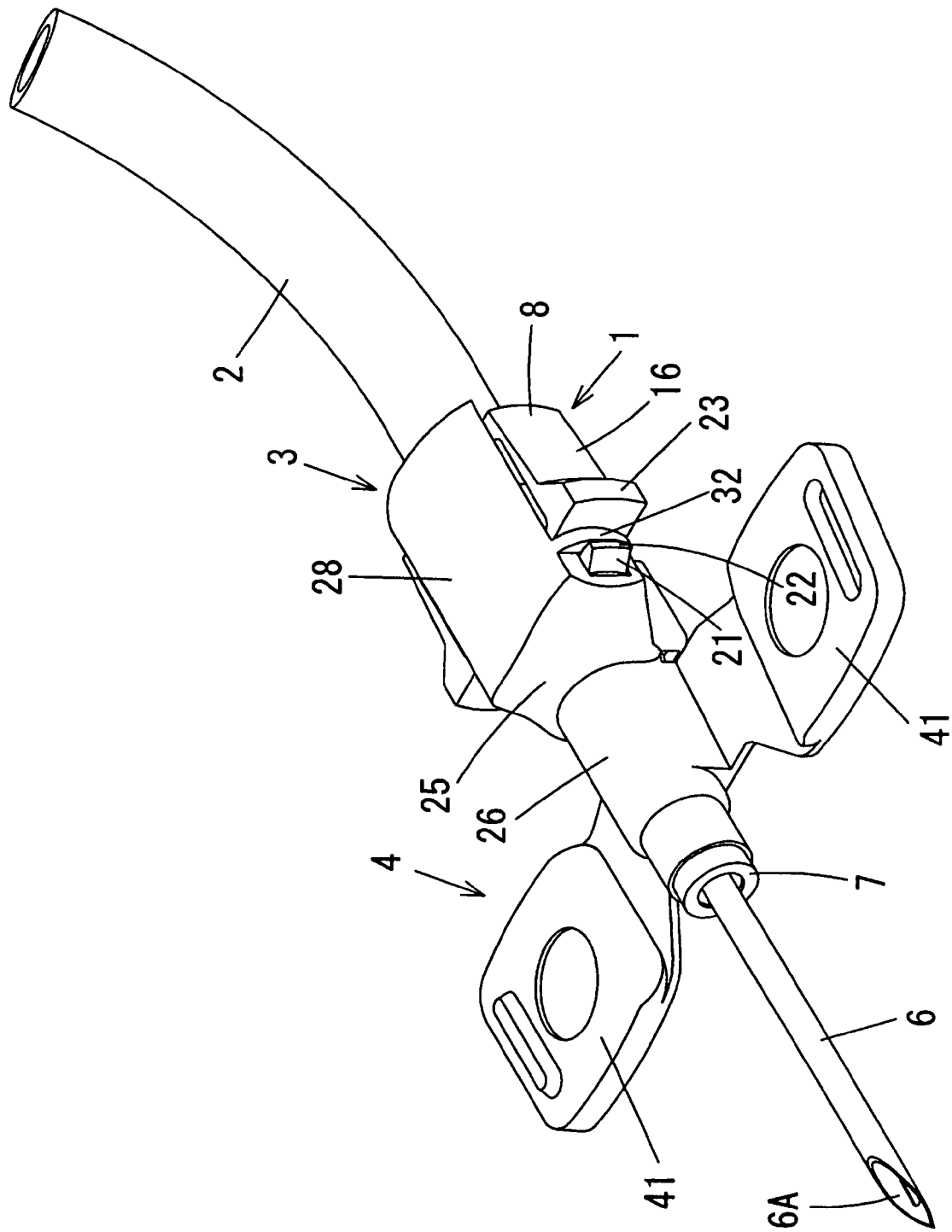
FIG. 29 is a perspective view illustrating Example 3 showing another embodiment of the present invention.
Figure 30:
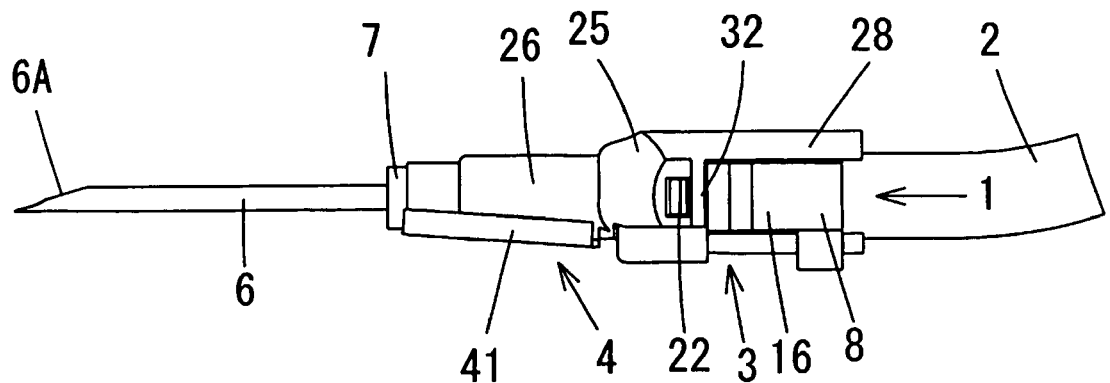
FIG. 30 is a side view of FIG. 29.
Figure 31:
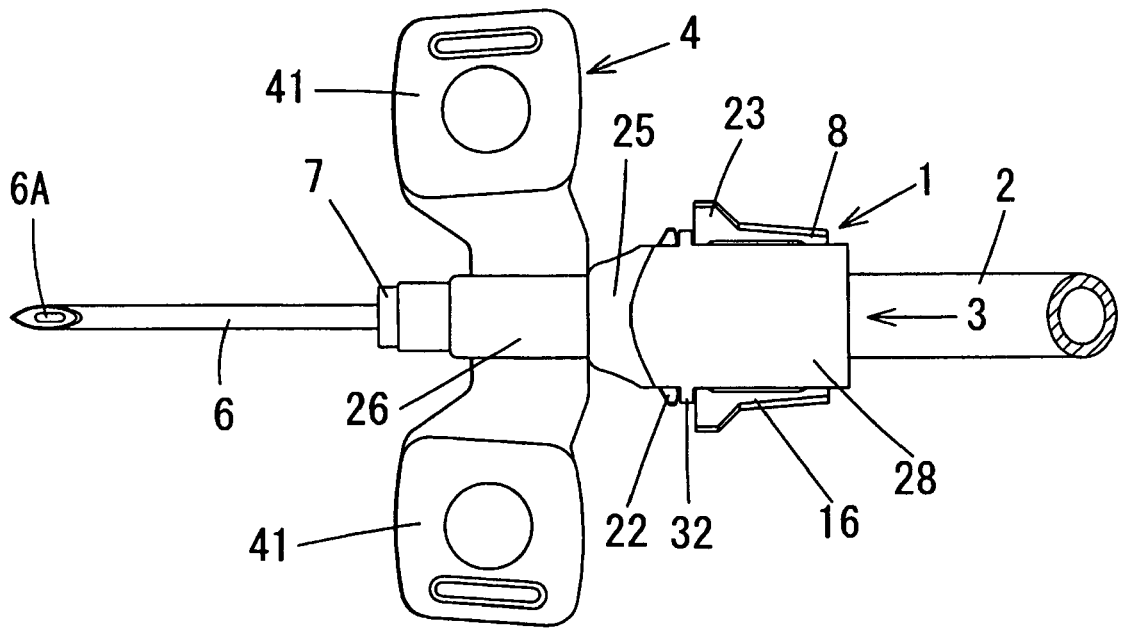
FIG. 31 is a plan view of FIG. 29.
Figure 32:
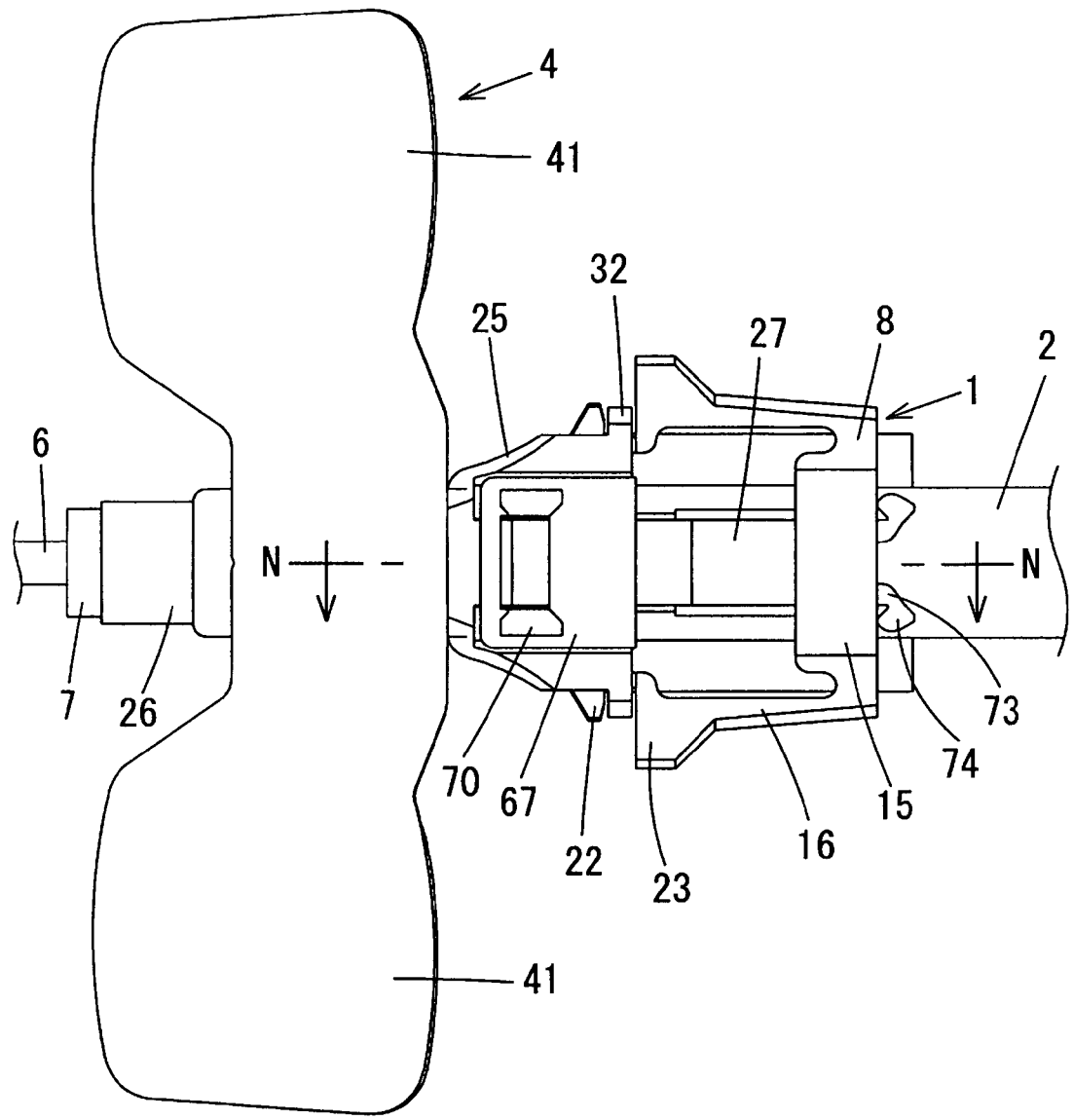
FIG. 32 is a bottom view of FIG. 29.
Figure 33:
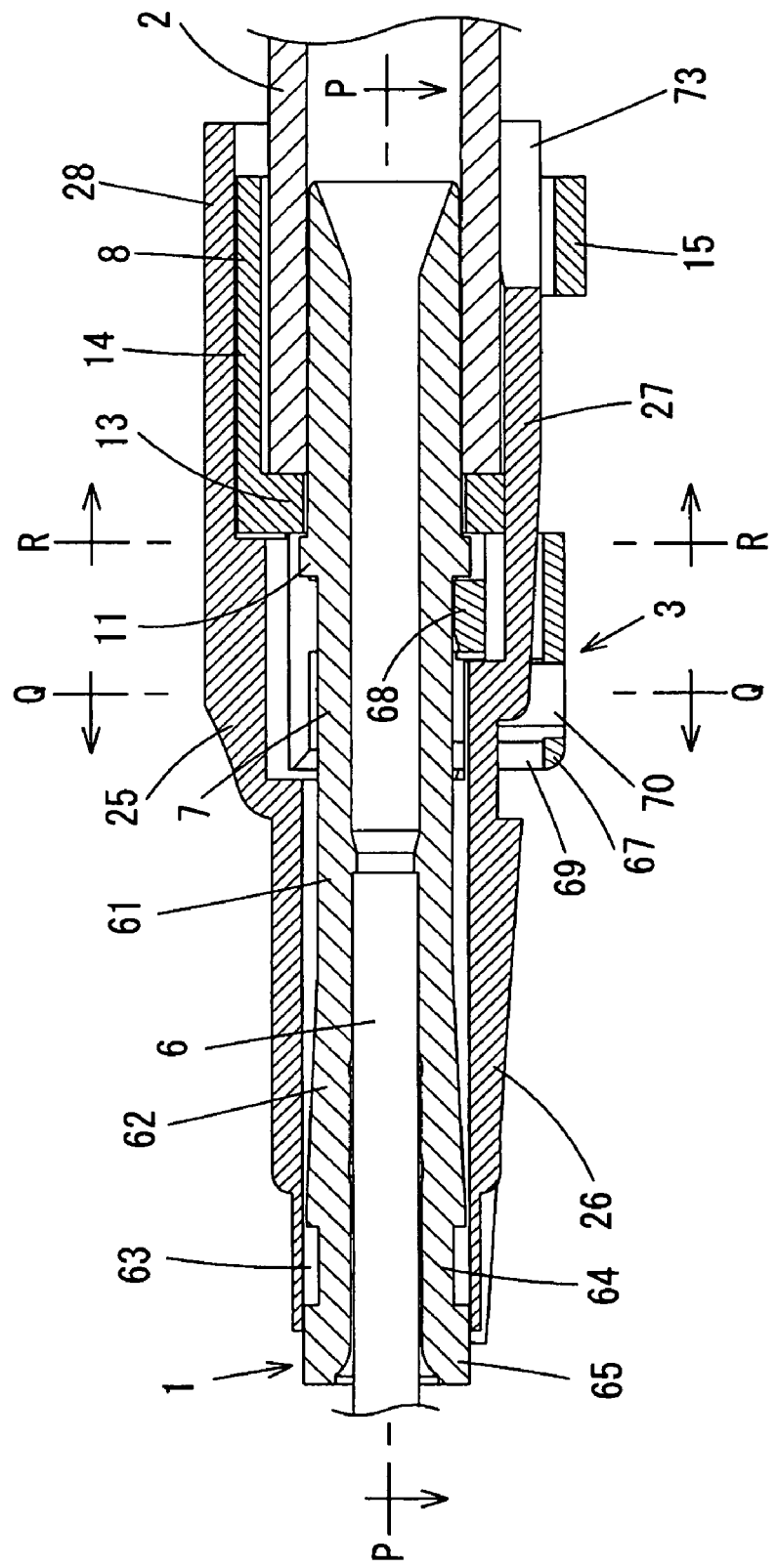
FIG. 33 is a cross-sectional view taken along the line N-N in FIG. 32.
Figure 34:
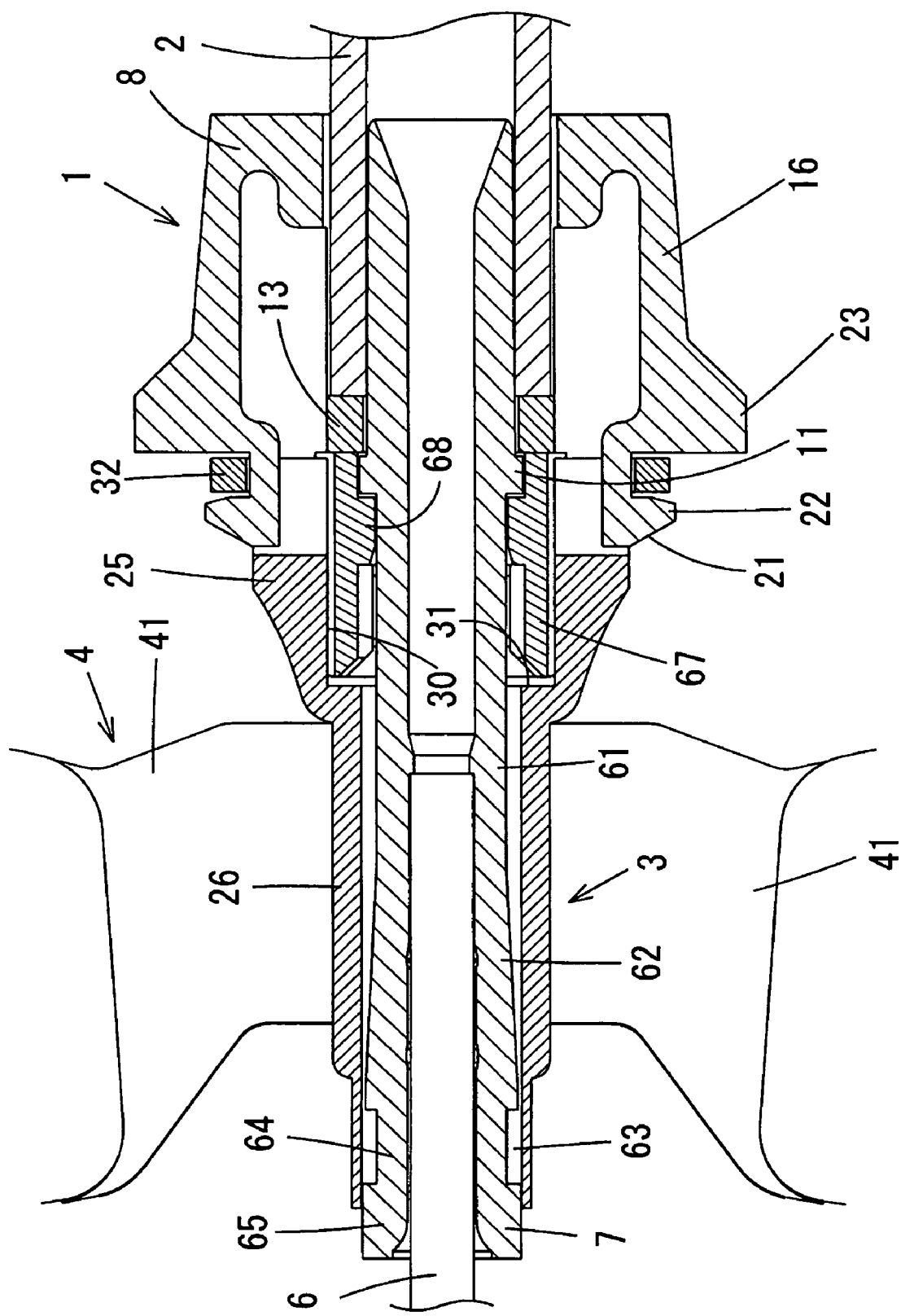
FIG. 34 is a cross-sectional view taken along the line P-P in FIG. 33.
Figure 35:
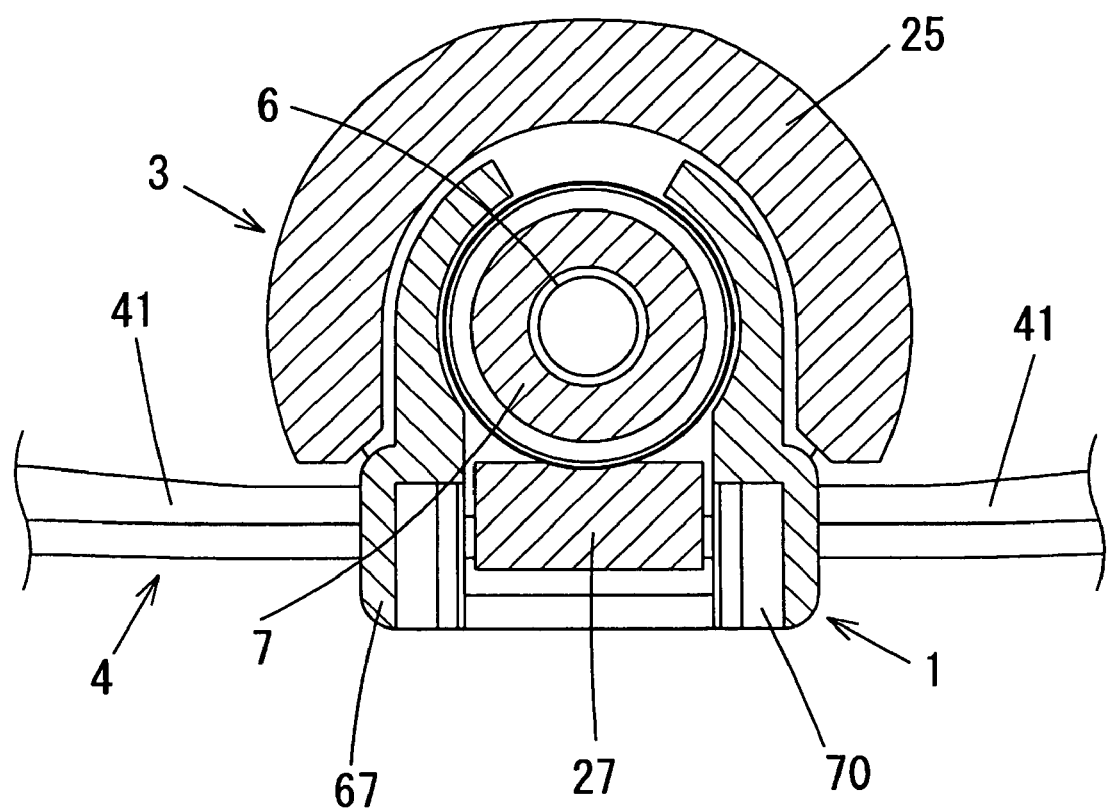
FIG. 35 is a cross-sectional view taken along the line Q-Q in FIG. 33.
Figure 36:
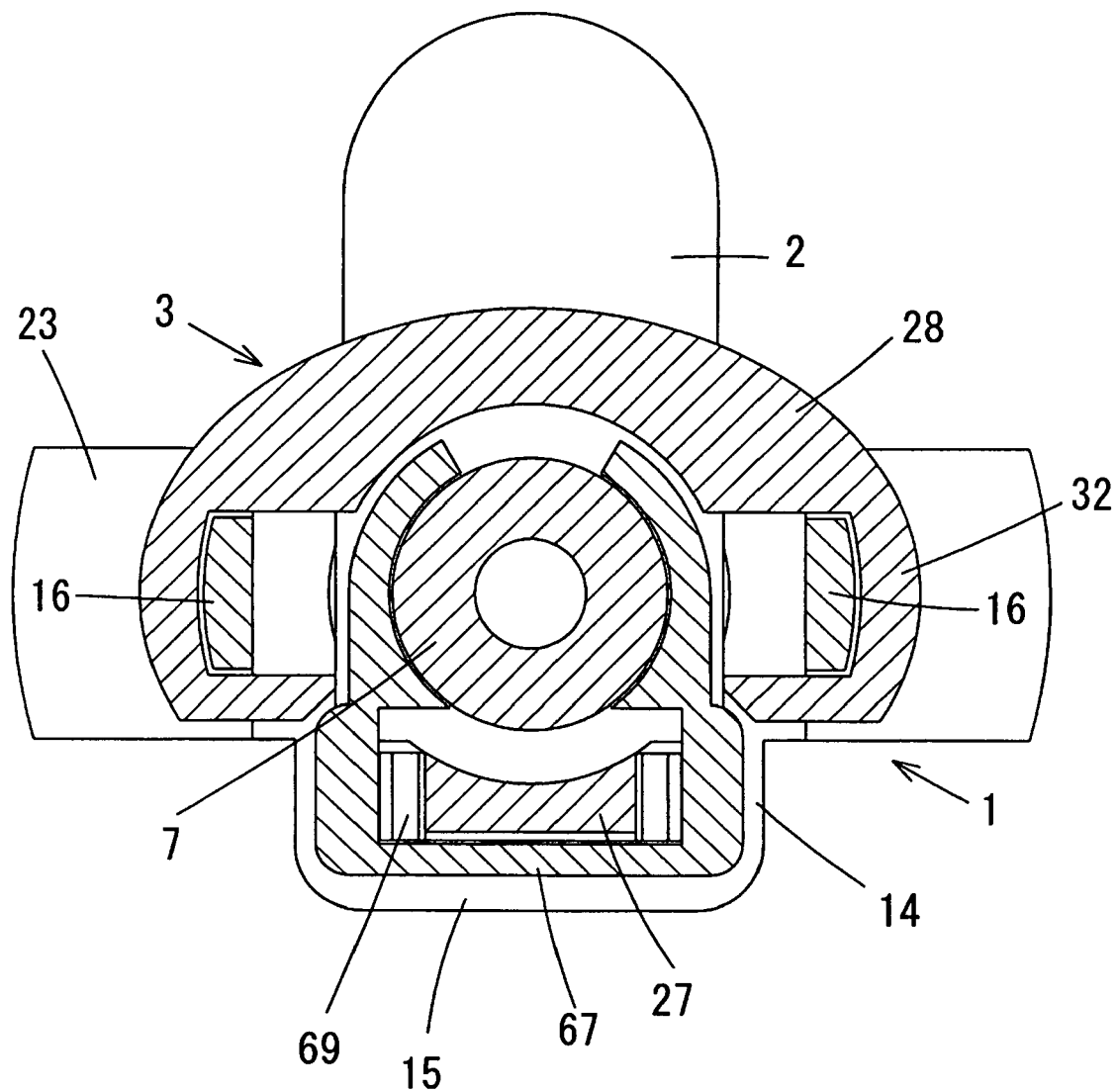
FIG. 36 is a cross-sectional view taken along the line R-R in FIG. 33.
Figure 37:
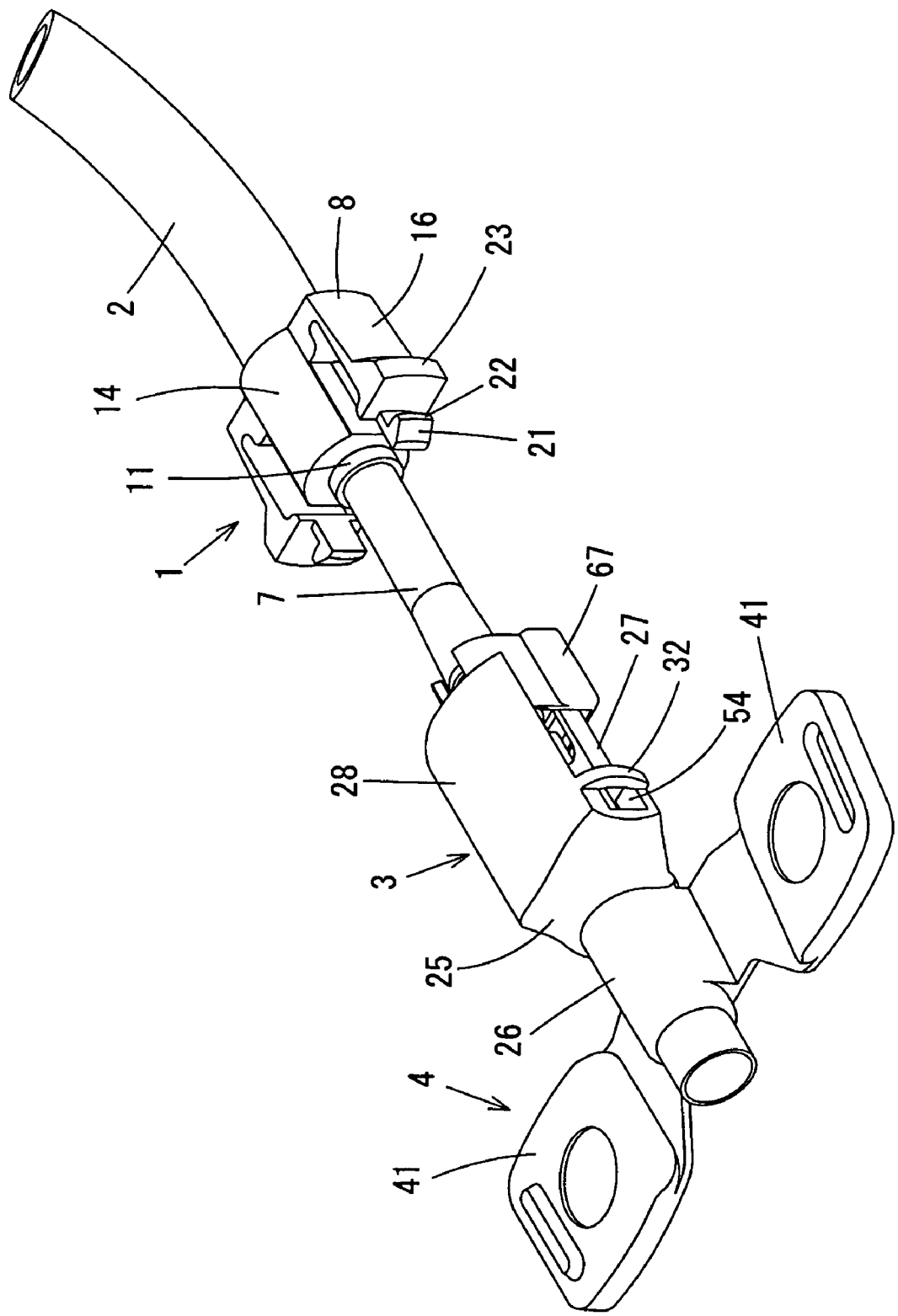
FIG. 37 is a perspective view illustrating a state in which the movable unit in FIG. 29 is positioned at the stored position.
Figure 38:
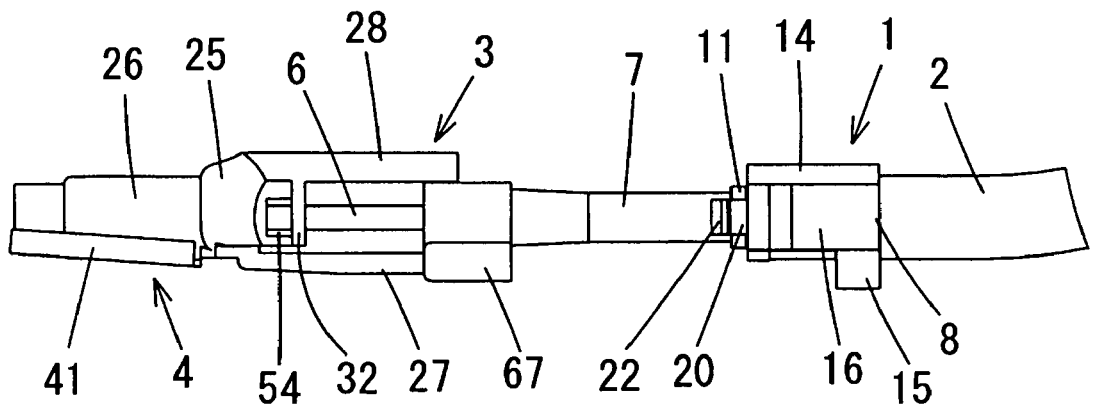
FIG. 38 is a side view of FIG. 37.
Figure 39:
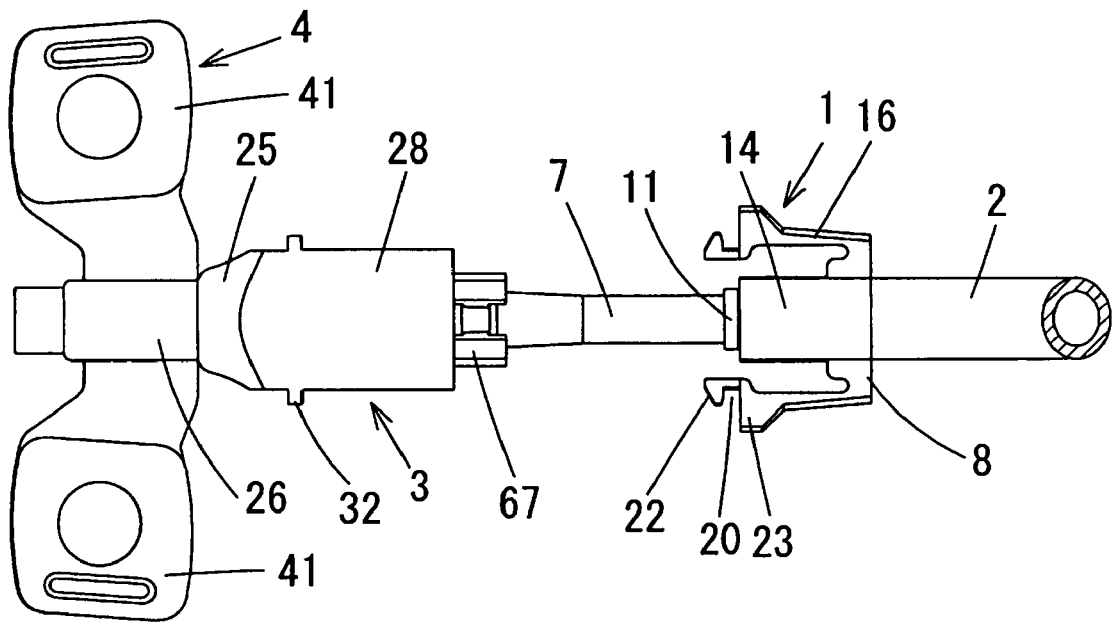
FIG. 39 is a plan view of FIG. 37.
Figure 40:
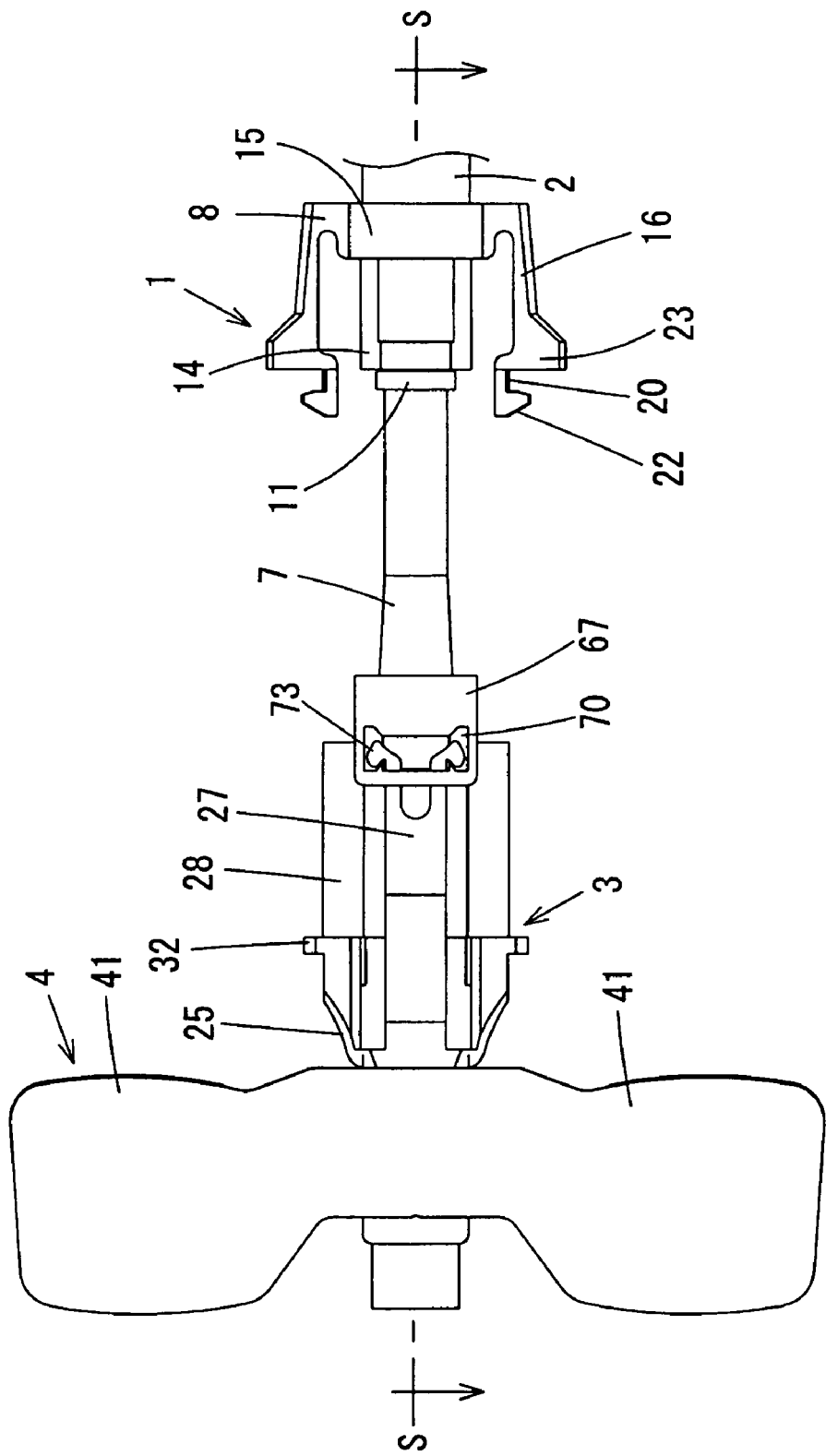
FIG. 40 is a bottom view of FIG. 37.
Figure 41:
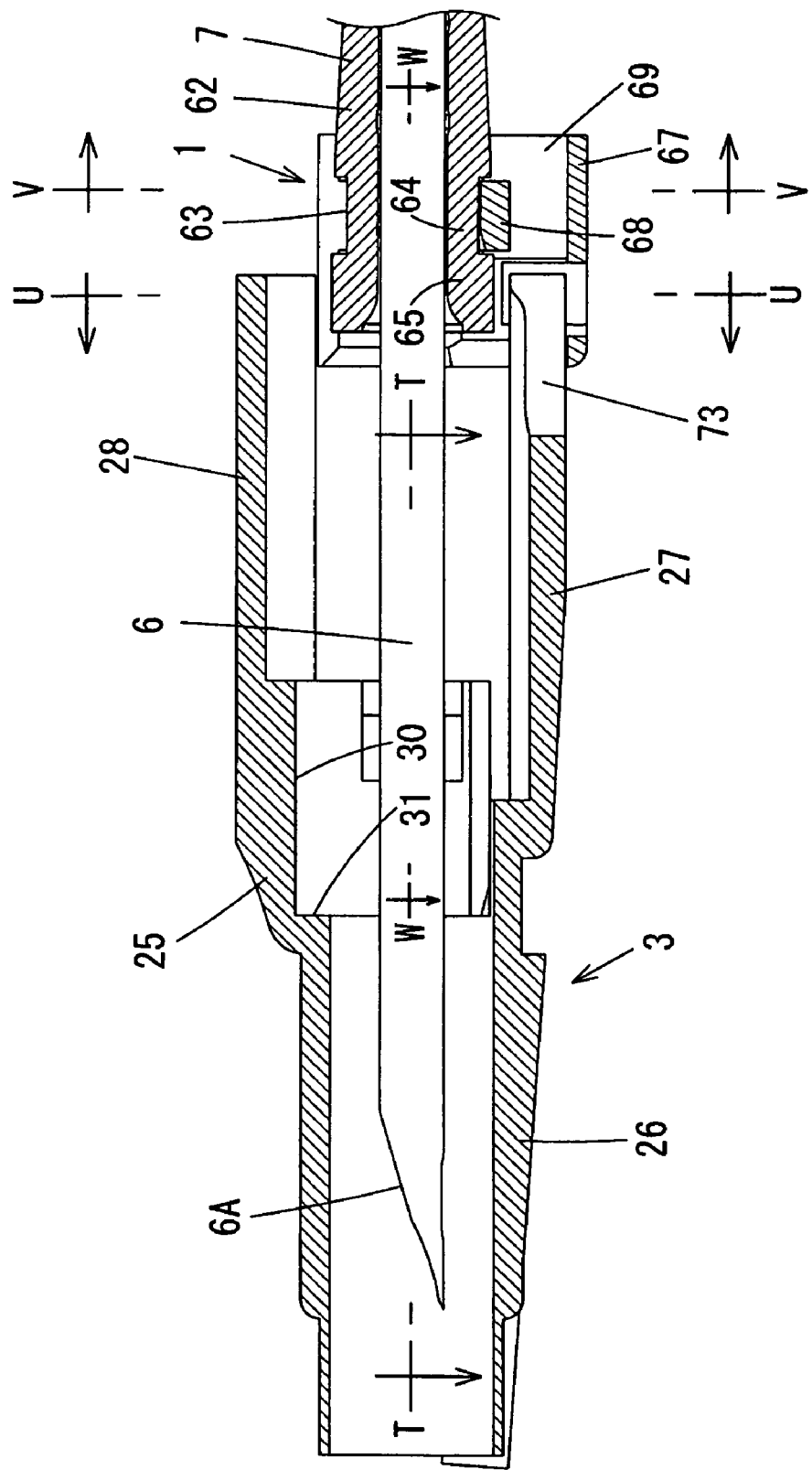
FIG. 41 is a cross-sectional view taken along the line S-S in FIG. 40.
Figure 42:
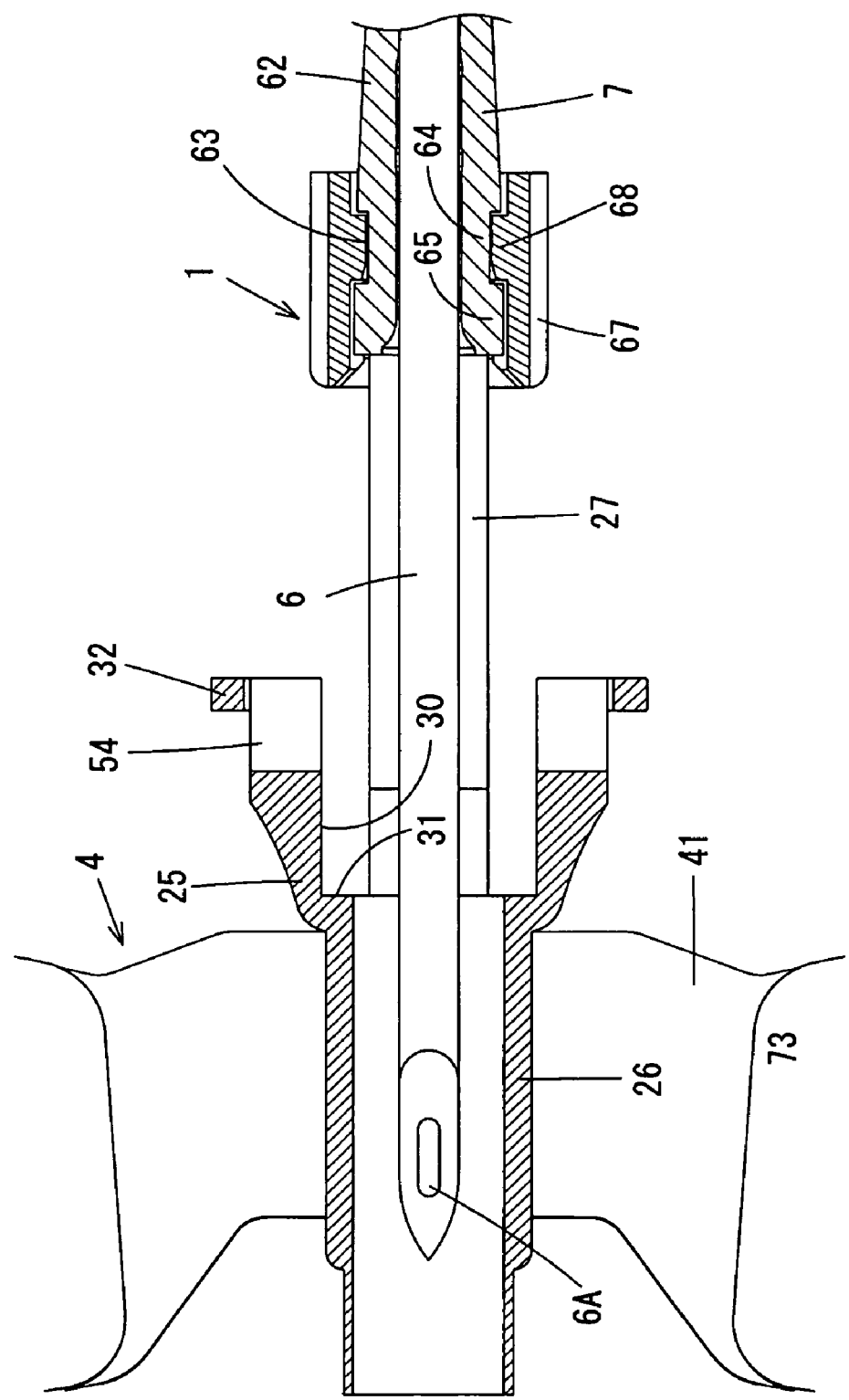
FIG. 42 is a cross-sectional view taken along the line T-T in FIG. 41.
Figure 43:
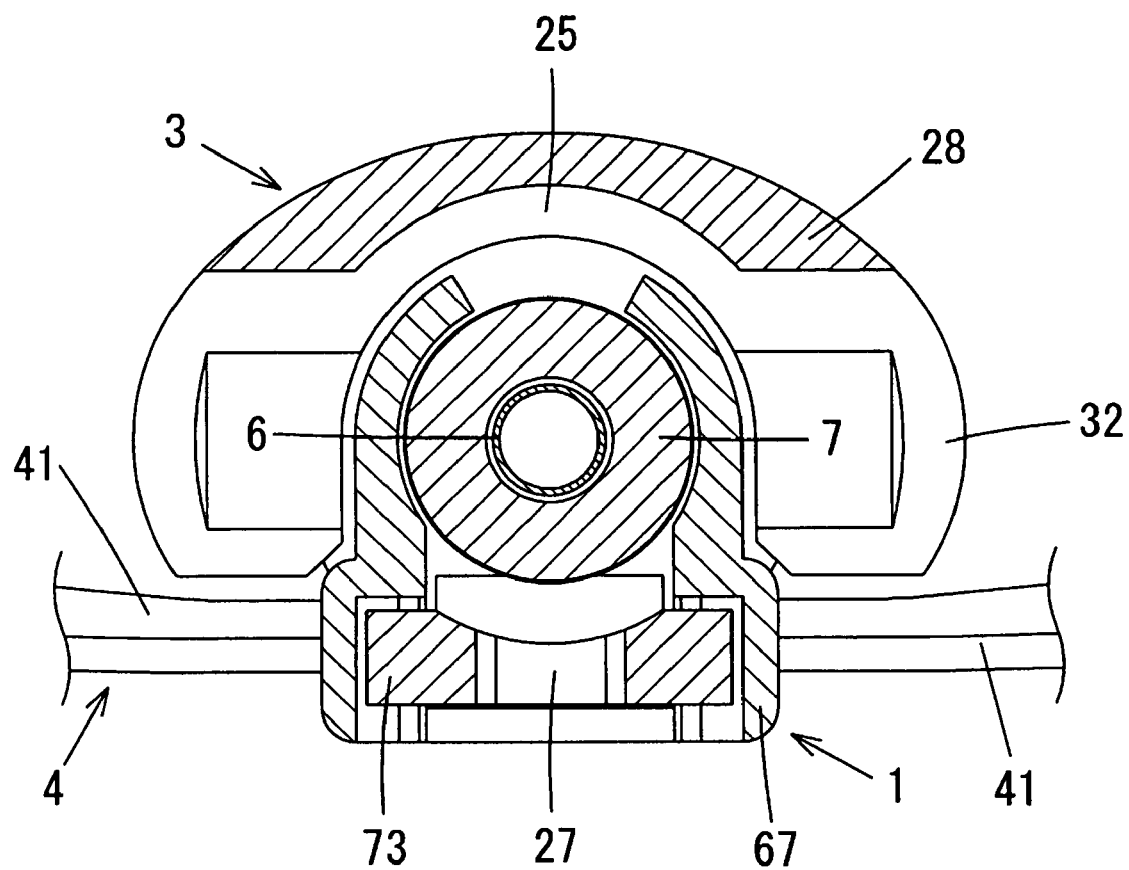
FIG. 43 is a cross-sectional view taken along the line U-U in FIG. 41.
Figure 44:
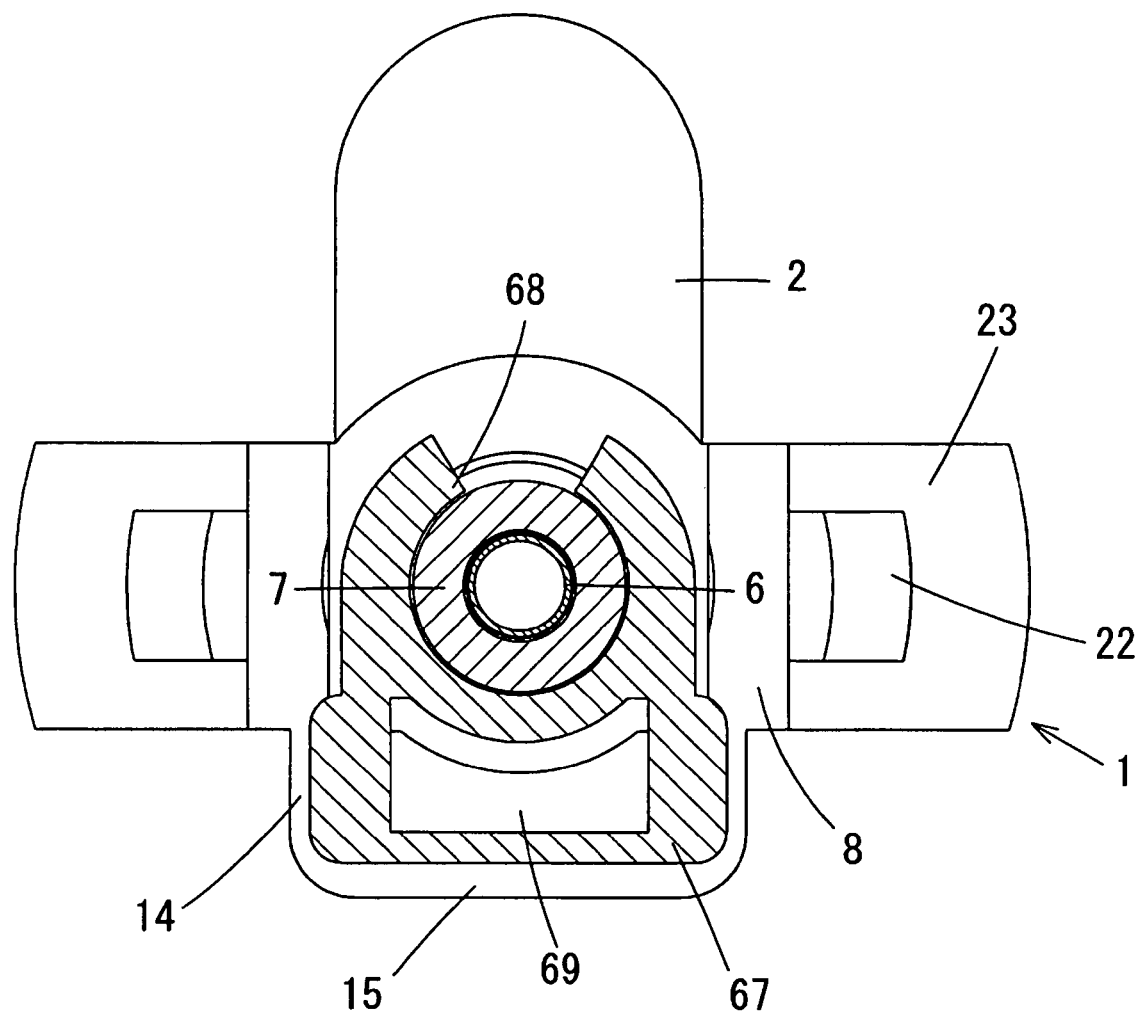
FIG. 44 is a cross-sectional view taken along the line V-V in FIG. 41.
Figure 45:
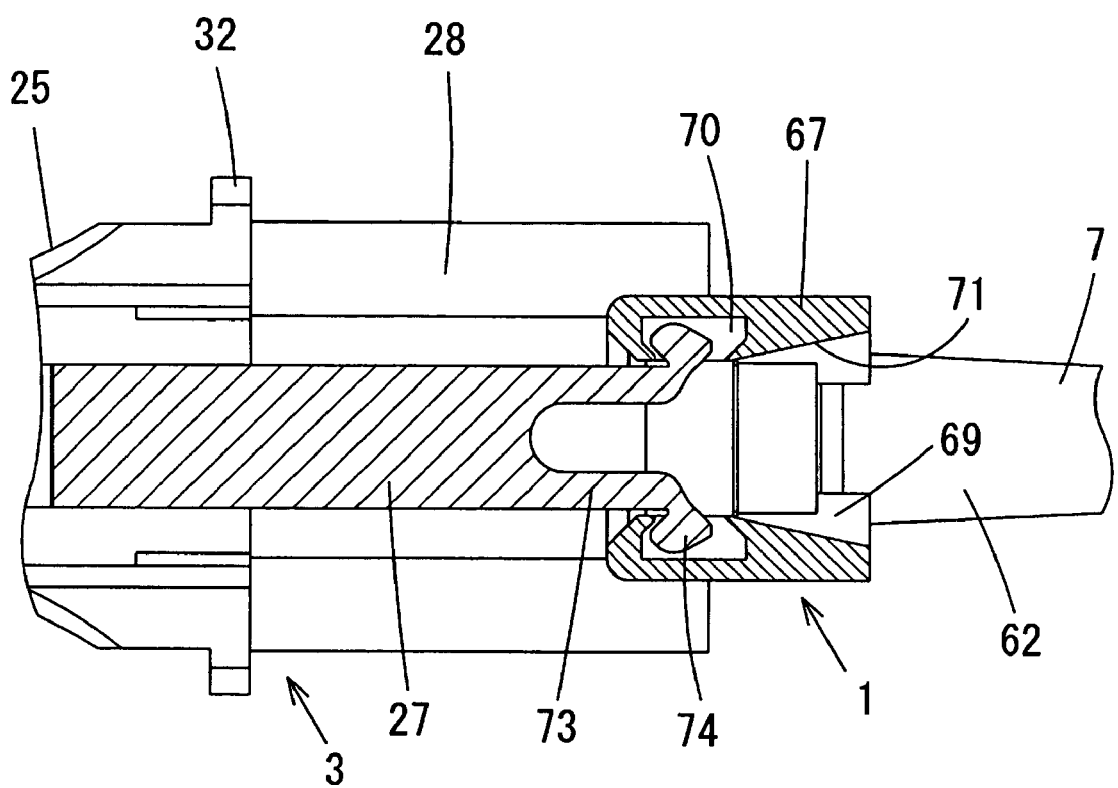
FIG. 45 is a cross-sectional view taken along the line W-W in FIG. 41.

The fixing wing 4 is formed separately from the protecting cylinder 26, includes an outer fitting portion 40 positioned at the widthwise center thereof and a pair of left and right wings 41 extending outward from the outer fitting portion 40, and is integrally formed of the same material as the hub 7. The outer fitting portion 40 is fitted on and secured to the protecting cylinder 26. The fixing wing 4 may be formed integrally with the protecting cylinder 26 as in Example 1. The back sides of the wings 41 may have surfaces having a plurality of concaves and convexes as shown in FIG. 18 to ensure the fixing to the patient.

In the configuration shown above, when the movable unit 1 is moved from the position in use shown in FIG. 15 to FIG. 21 to the stored position shown in FIG. 22 to FIG. 28, the pivoting arm 16 of the operating member 8 of the movable unit 1 is pressed downward via the operating portion 23, and the projection 22 is released from the engaging portion 32 of the lock portion 25 of the holder 3, and then the movable unit 1 is slid to the stored position, and only the front portion of the cannula 6 of the movable unit 1 including the blade point 6A is stored in the interior of the protecting cylinder 26 and the lock portion 25. In the case described above, the cover 28 covers the axial midsection of the cannula 6 on the left and right sides.

In addition, when sliding the movable unit 1, the slider 15 of the operating member 8 is moved within the guide groove 34 of the guide member 27 of the movable unit 1. However, since the retaining portion 19 of the slider 15 is in the state of being stored on the lower surface side of the guide member 27, the slider 15 is prevented from coming into contact with the hand or the arm of the patient.

When the slider 15 reaches the rear portion of the guide groove 34 while the movable unit 1 is sliding, the slider 15 comes into abutment with the both pivotal strips 38, resiliently deforms the both pivotal strips 38, and opens the same while bringing them into the outward pivotal movement, so that the sliding portion 18 of the slider 15 reaches the interior of the engaging groove 37 of the guide groove 34. Then, both the pivotal strips 38 restore to the original positions by a resiliently restoring force after the sliding portion 18 has passed over, so that the slider 15 is prevented from coming apart from the engaging groove 37. Accordingly, the movable unit 1 is fixed to the stored position.

EXAMPLE 3

Showing Another Embodiment

FIG. 29 to FIG. 45 illustrate Example 3 showing another embodiment of the present invention, which is a modification of Example 1. Different points will be described. The front side of the hub 7 with respect to the large-diameter portion 11 includes a small-diameter portion 61 being smaller in diameter than the large-diameter portion 11 and having a constant diameter in the axial direction, a tapered portion 62 tapered toward the rear, a peripheral grove portion 64 formed with an engaging groove 63 on the outer peripheral surface over the entire circumference thereof, and a constant diameter portion 65 having the same outer diameter as the front end of the tapered portion 62 and having a constant diameter in the axial direction, and the respective members are continuously formed in the axial direction.

The movable unit 1 includes a hollow fixing member 67. The fixing member 67 is formed into a substantially ring shape with the upper end portion thereof removed, and is formed integrally of a hard material having the resiliency like the hub 7. The fixing member 67 is fitted onto the front side of the hub 7 with respect to the large-diameter portion 11 and the guide member 27 so as to be slidable in the axial direction, and is formed on the inner peripheral surface thereof with an engaging projection 68 projecting radially inwardly. In a state in which the movable unit 1 is at the position in use, the engaging projection 68 comes into abutment with the large-diameter portion 11 of the hub 7 in terms of the axial direction, and opposes thereto with a slight gap interposed therebetween. The lower portion of the fixing member 67 is formed with a void portion 69 opening in the fore-and-aft direction and downward, and the lock portion 25 and the guide member 27 are inserted into the interior of the void portion 69. The front portion in the void portion 69 is formed on both the left and right side surfaces thereof with engaging recesses 70 recessed outward, and the inner surfaces of the both left and right sides of the rear portion in the void portion 69 is formed with an inclined surface 71 which is sloped inwardly toward the front.

The axial length of the guide member 27 is short, and the rear end thereof is substantially at the same position as the rear end of the cover 28 in terms of the axial direction. The rear portion of the guide member 27 is formed with a pair of left and right engaging claws 73. The engaging claws 73 are pivotable to the left and right through resilient deformation, and the rear end portions thereof are formed with outwardly projecting claws 74. The respective claws 74 engage the engaging recesses 70 of the fixing member 67 so as not to come apart therefrom when moving the fixing member 67 rearward, so that the fixing member 67 is fixed.

In the configuration described above, when the movable unit 1 is moved from the position in use shown in FIG. 29 to FIG. 36 to the stored position shown in FIG. 37 to FIG. 45, the pivoting arm 16 of the operating member 8 of the movable unit 1 is pivoted inwardly to cause the projection 22 of the operating member 8 to come apart from the engaging portion 32 of the lock portion 25 of the holder 3, and then the movable unit 1 is pulled rearward.

Accordingly, the movable unit 1 moves to the stored position at the rear together with the tube 2, and only the front portion including the blade point 6A of the cannula 6 is stored in the protecting cylinder 26. During this movement, the small-diameter portion 61 of the hub 7 and the tapered portion 62 slide with respect to the engaging projection 68 of the fixing member 67. Then, when the tapered portion 62 slides with respect to the engaging projection 68, the fixing member 67 resiliently deforms radially outward, and after the above-described sliding movement, the fixing member 67 is resiliently restored radially inwardly, and the engaging projection 68 of the fixing member 67 is dropped into the engaging groove 63 of the hub 7 and is engaged so as not to come apart therefrom, so that the hub 7 and the fixing member 67 are fixed.

After this fixing (or before this fixing), the inclined surface 71 of the fixing member 67 comes into abutment with the claws 74 of the engaging claws 73 of the guide member 27 and slides in the axial direction. Accordingly, the engaging claws 73 pivot inwardly through resilient deformation. When the sliding movement is terminated, the engaging claws 73 are resiliently restored and pivot outward, and the claws 74 engage the interior of the engaging recesses 70 of the fixing member 67 so as not come apart therefrom, so that the fixing member 67 is fixed at the stored position. In this manner, the movable unit 1 is fixed in the stored position.

In Example 3, the fixing member 67 is provided so as to be capable of sliding in the axial direction with respect to the hub 7, the lock portion 25 and the guide member 27, and engages the hub 7 and the guide member 27 so as not to come apart therefrom when the movable unit 1 is moved to the stored position, so that the movable unit 1 is fixed in the stored position. Therefore, the length of the guide member 27 may be shortened. Accordingly, when in use, the possibility that the medical person or the patient comes into contact with the guide member 27 may be reduced, and the possibility that the indwelling needle moves may be reduced, so that the possibility that a blood vessel or the like of the patient is damaged by the cannula 6 may be reduced.

In Example 1 and Example 3 showing the embodiments, the engaging portion is adapted to engage the engaging recess with respect to each other from the outside. However, it is also possible to configure the same to engage with respect to each other from the inside. In Example 2 showing the embodiment, the engaging portion is adapted to engage the engaging recess with respect to each other from above. However, on the contrary, it is also possible to configure the same to engage with respect to each other from below. Furthermore, although the guide member is not formed with the depressed portion in Example 2 and Example 3, it may be formed.

ADVANTAGE OF THE INVENTION

According to the present invention, an erroneous puncture accident by the cannula is prevented, and the possibility of damaging a blood vessel or the like of a patient by the blade point of the cannula being pivoted significantly downward is low even when the tube connected to the hub is moved upward in use.

According to the invention described in Claim 3, when the compression force in the axial direction is exerted into the guide member, the guide member is bent to form the upwardly curved protruding shape, and hence the blade point of the cannula is directed forward and obliquely downward. Therefore, the possibility that the cannula punctures medical person erroneously is low.

According to the invention described in Claim 5, the cover covers the axial midsection of the cannula. Therefore, even when blood or the like of the patient is attached to the axial midsection of the cannula, attachment of the blood or the like to medical person is prevented.

According to the invention described in Claim 6, the length of the guide member can be reduced, whereby the possibility that medical person or the patient come into contact with the guide member is reduced, and the possibility that the indwelling needle moves can be reduced, so that the possibility that the cannula accidentally damages a blood vessel or the like of the patient is also reduced.

The invention claimed is:

1. A winged indwelling needle comprising:
   (A) a movable unit having a cannula and a cylindrical hub to be connected to the cannula with the rear portion of the cannula inserted into the front portion thereof;
   (B) a tube which is connected to the rear portion of the hub and is brought into communication with the cannula,
   (C) a holder, and
   (D) a fixing wing having flexibility,
   the movable unit being provided on the holder so as to be capable of sliding in the axial direction, being capable of changing in position between a position in use and a stored position which is behind the position in use, and disengageably engaging the holder so as to be fixed to the holder when the movable unit is positioned at the position in use,
   wherein the holder includes:
   (a) a protecting cylinder which is positioned at the front portion of the holder, allows the cannula to project forwardly from the front end thereof when the movable unit is positioned at the position in use and stores only the front portion including a blade point of the cannula in the interior thereof when the movable unit is positioned at the stored position, and is provided with the fixing wing, and
   (b) a guide member positioned at the rear of the holder for guiding the sliding movement of the movable unit and fixing the movable unit by engaging the movable unit when the movable unit is positioned at the stored position, wherein the guide member (i) is formed into a plate shape having a planar shape on the upper and lower side, (ii) is exposed on the upper side, so that the tube is positioned above the guide member whereby the guide member allows the upward movement of the tube when the movable unit is positioned at the position in use, and (iii) is formed at the lower surface thereof with a depressed portion for allowing the guide member to bend upward so that it may curve when a compression force in the axial direction is exerted.

2. The winged indwelling needle according to claim 1, wherein the movable unit includes an operating member for operating the movable unit secured to the hub, wherein the operating member includes
   (E) a pivoting arm being capable of pivotal movement and disengageably engaging the holder through the pivotal movement when the movable unit is positioned at the position in use, and
   (F) a slider which is slidable in the axial direction with respect to the guide member, and
   wherein the guide member is provided at the rear portion thereof with engaging means for engaging the slider to fix the movable unit in the stored position.

3. The winged indwelling needle according to claim 2, wherein the holder includes:
   (G) a substantially ring shaped lock ,portion connected to the rear end portion of the protecting cylinder and the front end portion of the guide member and disengageably engaged with the pivoting arm, and
   (H) a cover extending rearward from the lock portion for covering the axial midsection of the cannula when the movable unit is positioned in the stored position.

4. The winged indwelling needle according to claim 1, wherein the movable unit includes:
   (I) the operating member for operating the movable unit secured to the hub, and
   (J) a fixing member which is provided on the hub and the guide member so as to be capable of sliding in the axial direction and is engaged with the hub and the guide member so as not to come apart therefrom when the movable unit is moved to the stored position, thereby fixing the movable unit at the stored position, and
   wherein the operating member includes a pivoting arm which is capable of the pivotal movement and is disengageably engaged with the holder through the pivotal movement when the movable unit is positioned at the position in use.

5. The winged indwelling needle according to claim 4, wherein the fixing member has a hollow shape,
   wherein the hub and the guide member are inserted into the interior of the fixing member,
   wherein the fixing member is formed with an engaging projection and an engaging recess in the interior thereof,
   wherein the hub is formed with an engaging groove with which the engaging projection is engageable so as not to come apart therefrom, and
   wherein the guide member is formed at the rear portion thereof with an engaging claw which is engageable with the engaging recess so as not to come apart therefrom.

* * * * *